US008710190B2

(12) United States Patent
Choo et al.

(10) Patent No.: US 8,710,190 B2
(45) Date of Patent: *Apr. 29, 2014

(54) HUMAN EMBRYONIC STEM CELL METHODS AND PODXL EXPRESSION

(75) Inventors: Andre Choo, Singapore (SG); Steve Oh, Singapore (SG)

(73) Assignee: Agency for Science, Technology and Research, Singapore (SG)

(*) Notice: Subject to any disclaimer, the term of this patent is extended or adjusted under 35 U.S.C. 154(b) by 0 days.

This patent is subject to a terminal disclaimer.

(21) Appl. No.: 13/445,705

(22) Filed: Apr. 12, 2012

(65) Prior Publication Data

US 2012/0219962 A1 Aug. 30, 2012

Related U.S. Application Data

(63) Continuation of application No. 12/282,164, filed as application No. PCT/SG2007/000064 on Mar. 6, 2007, now Pat. No. 8,173,374.

(60) Provisional application No. 60/778,913, filed on Mar. 6, 2006.

(51) Int. Cl.
*C07K 16/00* (2006.01)

(52) U.S. Cl.
USPC .................................................. 530/387.9

(58) Field of Classification Search
None
See application file for complete search history.

(56) References Cited

U.S. PATENT DOCUMENTS

| | | | | |
|---|---|---|---|---|
| 4,281,061 | A * | 7/1981 | Zuk et al. | 435/7.9 |
| 7,413,904 | B2 * | 8/2008 | Gold et al. | 435/455 |
| 8,173,374 | B2 * | 5/2012 | Choo et al. | 435/7.1 |
| 2005/0281828 | A1 | 12/2005 | Bowdish et al. | |
| 2006/0104974 | A1 | 5/2006 | Davis et al. | |
| 2006/0182724 | A1 | 8/2006 | Riordan | |
| 2006/0294607 | A1 | 12/2006 | Fitzhugh et al. | |
| 2007/0010011 | A1 | 1/2007 | Parsons et al. | |

FOREIGN PATENT DOCUMENTS

| | | |
|---|---|---|
| EP | 1970446 A1 | 9/2008 |
| WO | WO 95/25167 A1 | 9/1995 |
| WO | WO 99/10379 A1 | 3/1999 |
| WO | WO 2004/083406 A2 | 9/2004 |
| WO | WO 2004/109286 A2 | 12/2004 |
| WO | WO 2007/102787 A1 | 9/2007 |
| WO | WO 2007/149926 A1 | 12/2007 |
| WO | WO 2008/004990 A2 | 1/2008 |

OTHER PUBLICATIONS

Cai J et al., Development of antibodies to human embryonic stem cell antigens, *BMC Developmental Biology*, 5:26-32, 2005.

Cai J et al. 2006 "Assessing self-renewal and differentiation in human embryonic stem cell lines," *Stem Cells* 24:516-530.

Choo, A.B. et al. 2008 "Selection Against Undifferentiated Human Embryonic Stem Cells by a Cytotoxic Antibody Recognizing Podocalyxin-Like Protein-1" *Stem Cells* 26:1454-1463.

Doyonnas, R. et al. 2005 "Podocalyxin is a CD34-related marker of murine hematopoietic stem cells and embryonic erythroid cells" *Blood* 105(11):4170-4178.

Kershaw, D.B. et al., Molecular cloning and characterization of human podocalyxin-like protein: Orthologous relationship to rabbit PLCP1 and rat podocalyxin, *The Journal of Biological Chemistry*, 272:15708-15714, 1997.

Laslett, A. et al., "Transcriptional analysis of early lineage commitment in human embryonic stem cells," *BMC Developmental Biology*, 7:12-29, Mar. 2, 2007.

NCBI GenPept Accession No. AAC26544, anti BoNT/A seFv antibody [synthetic construct], 2001.

NCBI GenPept Accession No. ABC86095, Immunoglobulin kappa light chain [Mus Musculus], Feb. 2, 2006.

NCBI GenPept Accession No. AAB97461, anti-MUC1 antibody SM3 Ig heavy chain variable region [Mus Musculus], 1998.

Schopperle, W.M. et al. 2003 "Human embryonal carcinoma tumor antigen, Gp200/GCTM-2, is podocalyxin" *Biochemical and Biophysical Research Communications* 300:285-290.

Suonpää, P. et al. "Development of Early PCLP1-Expressing haematopoietic Cells within the Avian Dorsal Aorta" *Scandinavian Journal of Immunology* 62:218-223.

Abujarour et al., 2009, "Induced Pluripotent Stem Cells Free of Exogenous Reprogramming Facts," *Genome Biology*, 20: 220.

Choo et al., 2006, "Immortalized Feeders for the Scale-Up of Human Embryonic Stem Cells in Feeder and Feeder-Free Conditions," *Journal of Biotechnology*, 122: 130-141.

DeVries et al., 2008, "Reprogramming and Differentiation in Mammals: Motifs and Mechanisms," *Cold Spring Harbor Symposium*, 73: 33-38.

Fok et al., 2005, "Shear-Controlled Single-Step Mouse Embryonic Stem Cell Expansion and Empryoid Body-Based Differentiation," *Stem Cells*, 23: 1333-1342.

(Continued)

*Primary Examiner* — Michail Belyavskyi
(74) *Attorney, Agent, or Firm* — Knobbe, Martens, Olson & Bear, LLP

(57) ABSTRACT

A method of identifying an undifferentiated human embryonic stem cell in a sample which may contain such cells, the method comprising identifying the cell or cells within the sample that express podocalyxin-like protein (PODXL) on their surface. A method of isolating an undifferentiated human embryonic stem cell from a sample containing such cells, the method comprising isolating the cell or cells within the sample that express PODXL on their surface. Typically, the methods use an antibody which binds to PODXL. Undifferentiated human embryonic stem cells isolated by the method may be useful in cell therapy. Also, in particular, compositions of cells differentiated from a human embryonic stem cell but which composition has been depleted of undifferentiated human embryonic stem cells are provided which are useful in cell therapy.

5 Claims, 14 Drawing Sheets

(56) References Cited

OTHER PUBLICATIONS

Frauenschuch et al., 2007, "A Microcarrier-Based Cultivation System for Expansion of Primary Mesenchymal Stem Cells," *Biotechnol. Prog.*, 23: 187-193.

King et al., 2007, "Bioreactor Development for Stem Cell Expansion and Controlled Differentiation," *Current Opinion in Chemical Biology*, 11: 394-398.

Majino et al., 1995, "Apoptosis, Oncosis, and Necrosis: An Overview of Cell Death," *American Journal of Pathology*, 146: 3-15.

Newman et al., 2004, "Poly (D,L Lactic-co-glycolic acid) Microspheres as Biodegradable Microcarriers for Pluripotent Stem Cells," *Biomaterials*, 25: 5763-5771.

Nie et al., 2009, "Scalable Culture and Cryopreservation of Human Embryonic Stem Cells on Microcarriers," *Biotechnol. Prog.*, 25: 20-31.

Oh et al., 2006, "Human Embryonic Stem Cell Technology: Large Scale Cell Amplification and Differentiation," *Cytotechnology*, 50: 181-190.

Oh et al., 2009, "Long Term Microcarrier Suspension Cultures of Human Embryonic Stem Cells," *Stem Cell Research*, 2: 219-230.

Okita et al., 2007, "Generation of Germline-competent induced Pluripotent Stem Cells," *Nature*, 446: 313-318.

Phillips et al., 2008, "Attachment and Growth of Human Embryonic Stem Cells on Microcarriers," *Journal of Biotechnology*, 138: 24-32.

Schop et al., 2008, "Expansion of Mesenchymal Stem Cells Using a Microcarrier-based Cultivation System: Growth and Metabolism," *Journal of Tissue Engineering and Regenerative Medicine*, 2: 126-135.

Takahashi et al., 2006, "Induction of Pluripotent Stem Cells from Mouse Embryonic and Adult Fibroblast Cultures by Defined Factors," *Cells*, 126: 663-676.

Takahashi et al., 2007, "Induction of Pluripotent Stem Cells from Adult Human Fibroblasts by Defined Factors," *Cells*, 131: 1-12.

Tan et al., 2009, "mAb 84, a cytotoxic antibody that kills undifferentiated human embryonic stem cells via oncosis," *Stem Cells*, 27: 1792-1801.

Yamanaka, Shinya, 2009, "A Fresh Look at IPS Cells," *Cells*, 137: 13-17.

Yang et al., 2007, "Ex Vivo Expansion of Rat Bone Marrow Mesenchymal Stromal Cells on Microcarrier Beads in Spin Culture," *Biomaterials*, 28: 3110-3120.

Yu et al., 2007, "Induced Pluripotent Stem Cell Liens Derived from Human Somatic Cells," *Science*, 318: 1917-1920.

* cited by examiner

Scale Bar: 200 μm

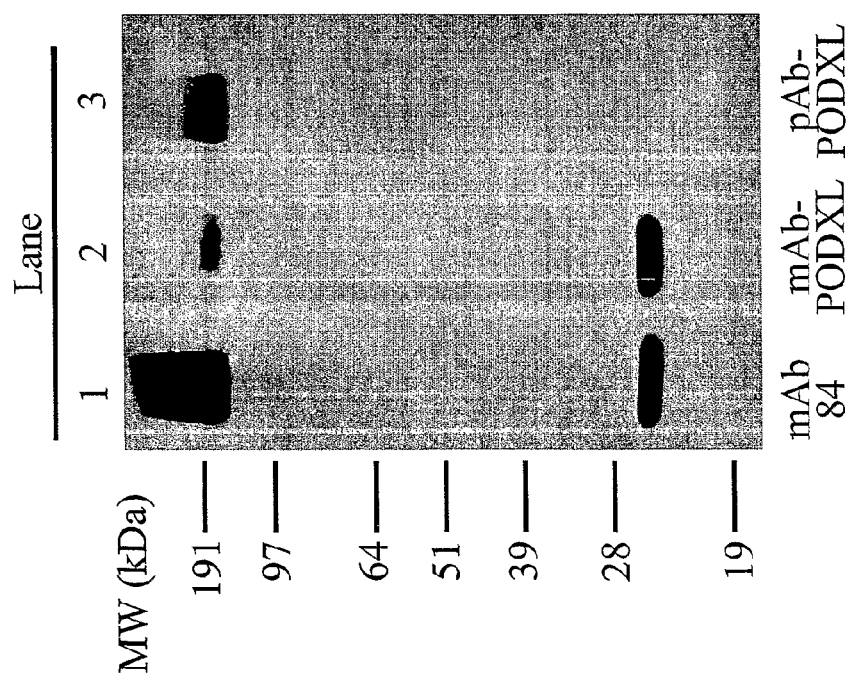

(O00592) Podocalyxin-like protein 1 precursor

```
  1  MRCALALSAL LLLLSTPPLL PSSPSPSPSP SPSQNATQTT TDSSNKTAPT
 51  PASSVTIMAT DTAQQSTVPT SKANEILASV KATTLGVSSD SPGTTTLAQQ
101  VSGPVNTTVA RGGGSGNPTT TIESPKSTKS ADTTTVATST ATAKPNTTSS
151  QNGAEDTTNS GGKSSHSVTT DLTSTKAEHL TTPHPTSPLS PRQPTLTHPV
201  ATPTSSGHDH LMKISSSSST VAIPGYTFTS PGMTTLPSS VISQRTQQTS
251  SQMPASSTAP SSQETVQPTS PATALRTPTL PETMSSSPTA ASTTHRYPKT
301  PSPTVAHESN WAKCEDLETQ TQSEKQLVLN LTGNTLCAGG ASDEKLISLI
351  CRAVKATFNP AQDKCGIRLA SVPGSQTVVV KEITIHTKLP AKDVYERLKD
401  KWDELKEAGV SDMKLGDQGP PEEAEDRFSM PLIITIVCMA SFLLVAALY
451  GCCHQRLSQR KDQQRLTEEL QTVENGYHDN PTLEVMETSS EMQEKKVVSL
501  NGELGDSWIV PLDNLTKDDL DEEEDTHL
```

Fig. 9B mAb 84 VL

The amino acids not underlined correspond to framework regions and underlined corresponds to CDRs.

```
1     ACGCCAGCTATTTAGGTGACACTATAGAATACTCAAGCTATGCATCCAACGCGTTGGGAG

61    CTCTCCCATATGGTCGACCTGCAGGCGGCCGCACTAGTGATTGACATTGAGCTCACCCAG
1                                                   D  I  E  L  T  Q

121   TCTCCAGCAATCATGTCTGCATCTCCAGGGGAGAAGGTCACCATGACCTGCAGTGCCAGC
7      S  P  A  I  M  S  A  S  P  G  E  K  V  T  M  T  C  S  A  S

181   TCAAGTGTAAATTACATGTACTGGTACCAGCAGAAGCCAGGATCCTCCCCCAGACTCCTG
27     S  S  V  N  Y  M  Y  W  Y  Q  Q  K  P  G  S  S  P  R  L  L

241   ATTTATGACACATCCAACCTGGCTTCTGGAGTCCCTGTTCGCTTCAGTGGCAGTGGGTCT
47     I  Y  D  T  S  N  L  A  S  G  V  P  V  R  F  S  G  S  G  S

301   GGGACCTCTTACTCTCTCACAATCAGCCGAATGGAGGCTGAAGATGCTGCCACTTATTAC
67     G  T  S  Y  S  L  T  I  S  R  M  E  A  E  D  A  A  T  Y  Y

361   TGCCAGCAGTGGAGTAGTTACCCGTACACGTTCGGAGGGGGGACCAAGCTGGAAATAAAA
87     C  Q  Q  W  S  S  Y  P  Y  T  F  G  G  G  T  K  L  E  I  K

421   CGGAATCCCGCGGCCATGGCGGCCGGGAGCATGCGACGTCGGGCCCAATTCGCCCTATAG
107    R

481   TGAGTCGTATTACAATTCACTGGCCGTCGTTTTACAACGTCGTGACTGGGAAAACCCTGG
541   CGTTACCCAACTTAATCGCCTTGCAGCACATCCCCCTTTCGCCAGCTGGCGTAATAGCGA
601   AGAGGCGCGCACCGATCGCCCTTCTCAACAGTTGCGCAGCCTGAATAGCGAATAGACGCG
661   CCCTGTAGCGGCGCATTATGCGCGGCGGGGTGTGGTGGTTACGCGCAGCGTGACCGCTAC
721   ACTTGTCAGCGCCCTAGCGCCGCTCCTTTCGCTTTCTTCCCTTCCTTTCTCGCCACGTTC
781   GCCGGCTTGCTCGTCAGG
```

Based on V Base and Kabat Numbering
NOT UNDERLINED: Framework
underlined: CDR

Fig. 11 mAb 84 VH

The amino acids not underlined correspond to framework regions and underlined corresponds to CDRs.

```
1    AGACGGCCAGTGATTGTATACGACTCACTATAGGGCGAATTGGGCCCGACGTCGCATGCT

61   CCCGGCCGCCATGGCCGCGGGATTCAGGTGCAGCTGCAGCAGTCAGGAGGAGGCTTGGTG
1                             Q  V  Q  L  Q  Q  S  G  G  G  L  V

121  CAACCTGGAGGATCCATGAAACTCTCCTGTGTTGCCTCTGGATTCACTTTCAGTAACTAC
13    Q  P  G  G  S  M  K  L  S  C  V  A  S  G  F  T  F  S  N  Y

181  TGGATGAACTGGGTCCGCCAGTCTCCAGAGAAGGGGCTTGAGTGGGTTGCTGAAATTAGA
33    W  M  N  W  V  R  Q  S  P  E  K  G  L  E  W  V  A  E  I  R

241  TTGAAATCTAATAATTATGCAACACATTATGCGGAGTCTGTGAAAGGGAGGTTCACCATC
53    L  K  S  N  N  Y  A  T  H  Y  A  E  S  V  K  G  R  F  T  I

301  TCAAGAGATGATTCCAAAAGTAGTGTCTACCTGCAAATGAACAACTTAAGAGCTGAAGAC
73    S  R  D  D  S  K  S  S  V  Y  L  Q  M  N  N  L  R  A  E  D

361  ACTGGCATTTATTACTGTACGGGGGAGAGGGCCTGGGGCCAAGGGACCACGGTCACCGTC
93    T  G  I  Y  Y  C  T  G  E  R  A  W  G  Q  G  T  T  V  T  V

421  TCCTCAAATCACTAGTGCGGCCGCCTGCAGGTCGACCATATGGGAGAGCTCCCAACGCGT
113   S  S

481  TGGATGCATAGCTTGAGTATTCTATAGTGTCACCTAAATAGCTTGGCGTAATCATGGTCA
541  TAGCTGTTTCCTGTGTGAAATTGTTATCCGCTCACAATTCCACACAACATACGAGCCGGA
601  AGCATAAAGTGTAAAGCCTGGGGTGCCTAATGAGTGAGCTAACTCACATTAATTGCGTTG
661  CGCTCACTGCCCGCTTTCCAGTCGGGAAACCTGTCGTGCCAGCTGCATTAATGAATCGGC
721  CAACGCGCGGGGAGAGGCGGTTTGCGTATTGGGCGCTCTTCGCTTCT
```

Based on V Base and Kabat Numbering
Not Underlined: Framework
Underlined: CDR

Fig. 12

SEQUENCE LISTING

<160> NUMBER OF SEQ ID NOS: 11

<210> SEQ ID NO 1
<211> LENGTH: 528
<212> TYPE: PRT
<213> ORGANISM: Homo sapiens
<220> FEATURE:
<221> NAME/KEY: MISC_FEATURE
<223> OTHER INFORMATION: amino acid sequence of Podocalyxin-like protein 1 precursor

<400> SEQUENCE: 1

Met Arg Cys Ala Leu Ala Leu Ser Ala Leu Leu Leu Leu Ser Thr
1               5                   10                  15

Pro Pro Leu Leu Pro Ser Ser Pro Ser Pro Ser Pro Ser Pro
            20                  25                  30

Ser Gln Asn Ala Thr Gln Thr Thr Asp Ser Ser Asn Lys Thr Ala
        35                  40                  45

Pro Thr Pro Ala Ser Ser Val Thr Ile Met Ala Thr Asp Thr Ala Gln
50                  55                  60

Gln Ser Thr Val Pro Thr Ser Lys Ala Asn Glu Ile Leu Ala Ser Val
65                  70                  75                  80

Lys Ala Thr Thr Leu Gly Val Ser Ser Asp Ser Pro Gly Thr Thr Thr
                85                  90                  95

Leu Ala Gln Gln Val Ser Gly Pro Val Asn Thr Thr Val Ala Arg Gly
                100                 105                 110

Gly Gly Ser Gly Asn Pro Thr Thr Thr Ile Glu Ser Pro Lys Ser Thr
            115                 120                 125

Lys Ser Ala Asp Thr Thr Thr Val Ala Thr Ser Thr Ala Thr Ala Lys
    130                 135                 140

Pro Asn Thr Thr Ser Ser Gln Asn Gly Ala Glu Asp Thr Thr Asn Ser
145                 150                 155                 160

Gly Gly Lys Ser Ser His Ser Val Thr Thr Asp Leu Thr Ser Thr Lys
                165                 170                 175

Ala Glu His Leu Thr Thr Pro His Pro Thr Ser Pro Leu Ser Pro Arg
                180                 185                 190

Gln Pro Thr Leu Thr His Pro Val Ala Thr Pro Thr Ser Ser Gly His
            195                 200                 205

Asp His Leu Met Lys Ile Ser Ser Ser Ser Thr Val Ala Ile Pro
    210                 215                 220

Gly Tyr Thr Phe Thr Ser Pro Gly Met Thr Thr Thr Leu Pro Ser Ser
225                 230                 235                 240

Val Ile Ser Gln Arg Thr Gln Gln Thr Ser Ser Gln Met Pro Ala Ser
                245                 250                 255

Ser Thr Ala Pro Ser Ser Gln Glu Thr Val Gln Pro Thr Ser Pro Ala
            260                 265                 270

Thr Ala Leu Arg Thr Pro Thr Leu Pro Glu Thr Met Ser Ser Ser Pro
    275                 280                 285

Thr Ala Ala Ser Thr Thr His Arg Tyr Pro Lys Thr Pro Ser Pro Thr
    290                 295                 300

Val Ala His Glu Ser Asn Trp Ala Lys Cys Glu Asp Leu Glu Thr Gln
305                 310                 315                 320

Thr Gln Ser Glu Lys Gln Leu Val Leu Asn Leu Thr Gly Asn Thr Leu
                325                 330                 335

Cys Ala Gly Gly Ala Ser Asp Glu Lys Leu Ile Ser Leu Ile Cys Arg

-continued

```
                    340                 345                 350
Ala Val Lys Ala Thr Phe Asn Pro Ala Gln Asp Lys Cys Gly Ile Arg
                355                 360                 365
Leu Ala Ser Val Pro Gly Ser Gln Thr Val Val Lys Glu Ile Thr
            370                 375                 380
Ile His Thr Lys Leu Pro Ala Lys Asp Val Tyr Glu Arg Leu Lys Asp
385                 390                 395                 400
Lys Trp Asp Glu Leu Lys Glu Ala Gly Val Ser Asp Met Lys Leu Gly
                405                 410                 415
Asp Gln Gly Pro Pro Glu Glu Ala Glu Asp Arg Phe Ser Met Pro Leu
            420                 425                 430
Ile Ile Thr Ile Val Cys Met Ala Ser Phe Leu Leu Val Ala Ala
            435                 440                 445
Leu Tyr Gly Cys Cys His Gln Arg Leu Ser Gln Arg Lys Asp Gln Gln
    450                 455                 460
Arg Leu Thr Glu Glu Leu Gln Thr Val Glu Asn Gly Tyr His Asp Asn
465                 470                 475                 480
Pro Thr Leu Glu Val Met Glu Thr Ser Ser Glu Met Gln Glu Lys Lys
                485                 490                 495
Val Val Ser Leu Asn Gly Glu Leu Gly Asp Ser Trp Ile Val Pro Leu
            500                 505                 510
Asp Asn Leu Thr Lys Asp Asp Leu Asp Glu Glu Asp Thr His Leu
            515                 520                 525

<210> SEQ ID NO 2
<211> LENGTH: 10
<212> TYPE: PRT
<213> ORGANISM: Artificial Sequence
<220> FEATURE:
<223> OTHER INFORMATION: Synthetic peptide

<400> SEQUENCE: 2

Ser Ala Ser Ser Ser Val Asn Tyr Met Tyr
1               5                   10

<210> SEQ ID NO 3
<211> LENGTH: 7
<212> TYPE: PRT
<213> ORGANISM: Artificial Sequence
<220> FEATURE:
<223> OTHER INFORMATION: Synthetic peptide

<400> SEQUENCE: 3

Asp Thr Ser Asn Leu Ala Ser
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic peptide

<400> SEQUENCE: 4

Gln Gln Trp Ser Ser Tyr Pro Tyr Thr
1               5

<210> SEQ ID NO 5
<211> LENGTH: 5
<212> TYPE: PRT
<213> ORGANISM: Artificial Sequence
<220> FEATURE:
```

<223> OTHER INFORMATION: Synthetic peptide

<400> SEQUENCE: 5

Asn Tyr Trp Met Asn
1               5

<210> SEQ ID NO 6
<211> LENGTH: 19
<212> TYPE: PRT
<213> ORGANISM: Artificial Sequence
<220> FEATURE:
<223> OTHER INFORMATION: Synthetic peptide

<400> SEQUENCE: 6

Glu Ile Arg Leu Lys Ser Asn Asn Tyr Ala Thr His Tyr Ala Glu Ser
1               5                   10                  15

Val Lys Gly

<210> SEQ ID NO 7
<211> LENGTH: 3
<212> TYPE: PRT
<213> ORGANISM: Artificial Sequence
<220> FEATURE:
<223> OTHER INFORMATION: Synthetic peptide

<400> SEQUENCE: 7

Glu Arg Ala
1

<210> SEQ ID NO 8
<211> LENGTH: 107
<212> TYPE: PRT
<213> ORGANISM: Mus musculus
<220> FEATURE:
<221> NAME/KEY: MISC_FEATURE
<223> OTHER INFORMATION: Amino acid sequence of the VL chain of mAb 84

<400> SEQUENCE: 8

Asp Ile Glu Leu Thr Gln Ser Pro Ala Ile Met Ser Ala Ser Pro Gly
1               5                   10                  15

Glu Lys Val Thr Met Thr Cys Ser Ala Ser Ser Ser Val Asn Tyr Met
                20                  25                  30

Tyr Trp Tyr Gln Gln Lys Pro Gly Ser Ser Pro Arg Leu Leu Ile Tyr
            35                  40                  45

Asp Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Tyr Pro Tyr Thr
                85                  90                  95

Phe Gly Gly Gly Thr Lys Leu Glu Ile Lys Arg
            100                 105

<210> SEQ ID NO 9
<211> LENGTH: 798
<212> TYPE: DNA
<213> ORGANISM: Mus musculus
<220> FEATURE:
<221> NAME/KEY: misc_feature
<223> OTHER INFORMATION: Polynucleotides encoding the VL chains of mAb
      84

<400> SEQUENCE: 9
acgccagcta tttaggtgac actatagaat actcaagcta tgcatccaac gcgttgggag     60

```
ctctcccata tggtcgacct gcaggcggcc gcactagtga ttgacattga gctcacccag      120
tctccagcaa tcatgtctgc atctccaggg gagaaggtca ccatgacctg cagtgccagc      180
tcaagtgtaa attacatgta ctggtaccag cagaagccag gatcctcccc cagactcctg      240
atttatgaca catccaacct ggcttctgga gtccctgttc gcttcagtgg cagtgggtct      300
gggacctctt actctctcac aatcagccga atggaggctg aagatgctgc cacttattac      360
tgccagcagt ggagtagtta cccgtacacg ttcggagggg ggaccaagct ggaaataaaa      420
cggaatcccg cggccatggc ggccgggagc atgcgacgtc gggcccaatt cgccctatag      480
tgagtcgtat tacaattcac tggccgtcgt tttacaacgt cgtgactggg aaaaccctgg      540
cgttacccaa cttaatcgcc ttgcagcaca tccccctttc gccagctggc gtaatagcga      600
agaggcgcgc accgatcgcc cttctcaaca gttgcgcagc ctgaatagcg aatagacgcg      660
ccctgtagcg gcgcattatg cgcggcgggg tgtggtggtt acgcgcagcg tgaccgctac      720
acttgtcagc gccctagcgc cgctcctttc gctttcttcc cttcctttct cgccacgttc      780
gccggcttgc tcgtcagg                                                    798
```

```
<210> SEQ ID NO 10
<211> LENGTH: 114
<212> TYPE: PRT
<213> ORGANISM: Mus musculus
<220> FEATURE:
<221> NAME/KEY: MISC_FEATURE
<223> OTHER INFORMATION: Amino acid sequence of the VH chain of mAb 84

<400> SEQUENCE: 10

Gln Val Gln Leu Gln Gln Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Gly Glu Arg Ala Trp Gly Gln Gly Thr Thr Val Thr Val
                100                 105                 110

Ser Ser
```

```
<210> SEQ ID NO 11
<211> LENGTH: 767
<212> TYPE: DNA
<213> ORGANISM: Mus musculus
<220> FEATURE:
<221> NAME/KEY: misc_feature
<223> OTHER INFORMATION: Polynucleotides encoding the VH chains of mAb
      84

<400> SEQUENCE: 11
agacggccag tgattgtata cgactcacta tagggcgaat tgggcccgac gtcgcatgct       60
cccggccgcc atggccgcgg gattcaggtg cagctgcagc agtcaggagg aggcttggtg      120
caacctggag gatccatgaa actctcctgt gttgcctctg gattcacttt cagtaactac      180
tggatgaact gggtccgcca gtctccagag aagggcttg agtgggttgc tgaaattaga      240
```

```
ttgaaatcta ataattatgc aacacattat gcggagtctg tgaaagggag gttcaccatc    300
tcaagagatg attccaaaag tagtgtctac ctgcaaatga acaacttaag agctgaagac    360
actggcattt attactgtac ggggagagg gcctggggcc aagggaccac ggtcaccgtc    420
tcctcaaatc actagtgcgg ccgcctgcag gtcgaccata tgggagagct cccaacgcgt    480
tggatgcata gcttgagtat tctatagtgt cacctaaata gcttggcgta atcatggtca    540
tagctgtttc ctgtgtgaaa ttgttatccg ctcacaattc cacacaacat acgagccgga    600
agcataaagt gtaaagcctg gggtgcctaa tgagtgagct aactcacatt aattgcgttg    660
cgctcactgc ccgctttcca gtcgggaaac ctgtcgtgcc agctgcatta atgaatcggc    720
caacgcgcgg ggagaggcgg tttgcgtatt gggcgctctt cgcttct                 767
```

HUMAN EMBRYONIC STEM CELL METHODS AND PODXL EXPRESSION

REFERENCE TO SEQUENCE LISTING

A Sequence Listing submitted as an ASCII text file via EFS-Web is hereby incorporated by reference in accordance with 35 U.S.C. §1.52(e). The name of the ASCII text file for the Sequence Listing is 13239777_1.TXT, the date of creation of the ASCII text file is May 8, 2012, and the size of the ASCII text file is 10.5 KB.

FIELD OF THE INVENTION

The present invention relates to methods for identifying undifferentiated human embryonic stem cells in, and isolating them from, a sample; and to methods for depleting such cells in a sample. The present invention also relates to kits of parts useful in such methods.

DESCRIPTION OF THE RELATED ART

Undifferentiated human embryonic stem cells have various uses in medicine, for example in tissue regeneration and repair, and it is believed that they will become increasingly important in the future. Today, donated organs and tissues are often used to replace ailing or destroyed tissue, but the need for transplantable tissues and organs far outweighs the available supply. Stem cells, particularly human embryonic stem cells, which can be directed to differentiate into specific cell types, offer the possibility of a renewable source of replacement cells and tissues to treat diseases including Parkinson's and Alzheimer's diseases, spinal cord injury, stroke, burns, heart disease, diabetes, osteoarthritis, and rheumatoid arthritis.

At present, the tests used to identify human embryonic stem cells include:

growing and subculturing the stem cells for many months. This ensures that the cells are capable of long-term self-renewal. The cultures are inspected through a microscope to see that the cells look healthy and remain undifferentiated.

using specific techniques to determine the presence of surface markers that are found only on undifferentiated cells. Another important test is for the presence of a protein called Oct-4, which undifferentiated cells typically make. Oct-4 is a transcription factor, meaning that it helps turn genes on and off at the right time, which is an important part of the processes of cell differentiation and embryonic development.

testing whether the human embryonic stem cells are pluripotent by 1) allowing the cells to differentiate spontaneously in cell culture; 2) manipulating the cells so they will differentiate to form specific cell types; or 3) injecting the cells into an immunosuppressed mouse to test for the formation of a benign tumor called a teratoma. Teratomas typically contain a mixture of many differentiated or partly differentiated cell types—an indication that the embryonic stem cells are capable of differentiating into multiple cell types.

Although undifferentiated human embryonic stem cells themselves may be used in cell therapy, it is considered to be beneficial to use cells which have started to differentiate, or are differentiated, compared to the human embryonic stem cell. Methods of encouraging undifferentiated human embryonic stem cells to differentiate into particular cell lineages are well known in the art. Once this differentiation process has started or proceeded, it is beneficial to remove or destroy undifferentiated human embryonic stem cells which may otherwise foam undesirable teratomas.

Thus, it can be seen that it is useful to identify or isolate undifferentiated human embryonic stem cells (since they can be used themselves in therapy or can be encouraged to differentiate into a particular cell lineage which can be used in therapy). It is also useful to remove or destroy undifferentiated human embryonic stem cells from a mixture of cells where some of the cells have started to differentiate, or are differentiated, since these differentiated cells are useful in therapy.

There remains a need for further ways of identifying undifferentiated human embryonic stem cells. The present inventors have now found that podocalyxin-like protein-1 precursor is a marker of undifferentiated human embryonic stem cells.

The listing or discussion of a prior-published document in this specification should not necessarily be taken as an acknowledgement that the document is part of the state of the art or is common general knowledge.

SUMMARY OF THE INVENTION

A first aspect of the invention provides a method of identifying an undifferentiated human embryonic stem cell in a sample which may contain such cells, the method comprising identifying the cell or cells within the sample that express podocalyxin-like protein-1 precursor (PODXL) on their surface.

The method may be used to assess whether a particular sample contains undifferentiated human embryonic stem cells and, if so, how many such cells. Thus, the invention includes the quantification of undifferentiated human embryonic stem cells.

A second aspect of the invention provides a method of isolating an undifferentiated human embryonic stem cell from a sample containing such cells, the method comprising isolating the cell or cells within the sample that express PODXL on their surface.

The method may be used to provide an enriched or substantially isolated composition of undifferentiated human embryonic stein cells. Such a composition may be used in various ways, for example it may itself be used in cell therapy as discussed in more detail below or it may be used as a source of cells which are then encouraged to differentiate into a particular cell lineage which is useful for a particular therapy, or it may be used to (in vitro or in vivo) investigate the factors which allow for the human embryonic stem cell to differentiate into other cells.

Typically, the enriched composition of human embryonic stem cells contains at least 50% of the cells as undifferentiated human embryonic stem cells, preferably at least 70% or at least 90% or at least 95%. Preferably, all of the cells in the composition are the said undifferentiated human embryonic stem cells.

A third aspect of the invention provides a method of removing an undifferentiated human embryonic stem cell from a sample containing such cells, the method comprising removing from the sample the cell or cells that express PODXL on their surface.

The removed cells may form a composition of human embryonic stem cells as in the second aspect of the invention. Also, the sample, from which the human embryonic stem cells have been removed, may be useful in therapy as discussed in more detail below.

A fourth aspect of the invention provides a method of destroying an undifferentiated human embryonic stem cell in a sample containing such cells, the method comprising destroying the cell or cells in the sample that express PODXL on their surface.

The destruction or killing of undifferentiated human embryonic stem cells in a sample is useful because, as discussed below, it is sometimes beneficial to remove undifferentiated human embryonic stem cells from a mixture of undifferentiated and differentiated cells.

The sample may be any sample which contains, or is suspected of containing, one or more undifferentiated human embryonic stem cells. Suitable samples include a human embryo or human embryonic tissue. Other suitable samples include a sample of cells grown in vitro.

In relation to the third and fourth aspects of the invention it is particularly preferred that the sample is one in which undifferentiated human embryonic stem cells have been encouraged (or promoted) to differentiate into particular cell lineages and therefore the sample may contain a mixture of undifferentiated and differentiated cells (because differentiation is currently not an efficient process). Typically in such a sample the undifferentiated human embryonic stem cells constitute a few % of the total number of cells. Typically, the differentiated cells in the sample may be cardiomyocytes, pancreatic islets, neuronal progenitor cells or mesenchymal stein cells which are derived (by differentiation) from human embryonic stem cells.

DETAILED DESCRIPTION OF THE PREFERRED EMBODIMENT

Removal (or destruction) of the undifferentiated human embryonic stem cells from (or in) such a sample will be useful prior to the clinical application of the sample which contains differentiated cells because, potentially, the undifferentiated cells can form undesirable teratomas. Typically, at least 95% of the undifferentiated human embryonic stem cells are removed or destroyed. Preferably, all of the said cells are removed or destroyed.

Destruction or killing of the undifferentiated cells in the sample is preferred to their removal so as to minimise additional steps in cell processing or separation. Also, it is believed that killing may be a more "absolute" form of cell removal.

The amino acid sequence of Podocalyxin-like protein 1 precursor is given in FIG. 9B (SEQ ID NO: 1) and is also found in Accession No O00592 of the NCBI protein sequence database accessible through EntrezPubMed (see also Kershaw et al (1997) *J. Biol. Chem.* 272, 15708-15714). It is also called PCLP1 and PODXL. For convenience, it will be called PODXL hereafter. It will be appreciated that the marker which is used in the methods of the invention is the PODXL which is found in nature in undifferentiated human embryonic stem cells. The PODXL therefore may have the precise sequence given in FIG. 9B, or it may be a naturally occurring variant thereof. For example, according to O00592, R is a variant for the T at residue 62, and S is a variant of the L at residue 196.

In a particularly preferred embodiment of the first, second and third aspects of the invention, the sample is contacted with a binding moiety, which binding moiety binds to PODXL and the said human embryonic stem cell is identified in or isolated from or removed from the sample by virtue of it being bound to the binding moiety.

According to O00592, PODXL is a 528 residue glycosylated cell surface polypeptide, of which residues 1-22 are a signal peptide, and residues 23-528 represent the mature protein. Residues 23-431 are believed to be the extracellular portion of the protein and residues 432-452 are the transmembrane region.

Residues 23-304 represent a Ser/Thr rich region. It is preferred if the binding moiety which binds to PODXL binds to the extracellular region of PODXL, for example within the Ser/Thr rich region, or outside of this region.

Conveniently, the said binding moiety is an antibody by which term we include a fragment or derivative thereof, or a synthetic antibody or synthetic antibody fragment.

Antibodies which will bind to PODXL are already known. For example, goat IgG specific for human podocalyxin, which polyclonal antisera binds to the extracellular domain, is available from R&D Systems, Inc under catalogue number AF1658. Also, a monoclonal anti-human podocalyxin antibody (mouse $IgG_{2A}$) is available from R&D Systems, Inc under catalogue number MAB1658. In any case, with today's techniques in relation to monoclonal antibody technology, antibodies can be prepared to most antigens. The antigen-binding portion may be a part of an antibody (for example a Fab fragment) or a synthetic antibody fragment (for example a single chain Fv fragment [ScFv]). Suitable monoclonal antibodies to selected antigens may be prepared by known techniques, for example those disclosed in "*Monoclonal Antibodies: A manual of techniques*", H Zola (CRC Press, 1988) and in "*Monoclonal Hybridoma Antibodies: Techniques and Applications*", J G R Hurrell (CRC Press, 1982).

Chimaeric antibodies are discussed by Neuberger et al (1988, 8*th International Biotechnology Symposium* Part 2, 792-799).

Polyclonal antibodies are useful in the methods of the invention. Monospecific polyclonal antibodies are preferred. Suitable polyclonal antibodies can be prepared using methods well known in the art.

Fragments of antibodies, such as Fab and $Fab_2$ fragments may also be used as can genetically engineered antibodies and antibody fragments.

The variable heavy ($V_H$) and variable light ($V_L$) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parented antibody (Morrison et al (1984) *Proc. Natl. Acad. Sci. USA* 81, 6851-6855).

That antigenic specificity is conferred by variable domains and is independent of the constant domains is known from experiments involving the bacterial expression of antibody fragments, all containing one or more variable domains. These molecules include Fab-like molecules (Better et al (1988) *Science* 240, 1041); Fv molecules (Skerra et al (1988) *Science* 240, 1038); single-chain Fv (ScFv) molecules where the $V_H$ and $V_L$ partner domains are linked via a flexible oligopeptide (Bird et al (1988) *Science* 242, 423; Huston et al (1988) *Proc. Natl. Acad. Sci. USA* 85, 5879) and single domain antibodies (dAbs) comprising isolated V domains (Ward et al (1989) *Nature* 341, 544). A general review of the techniques involved in the synthesis of antibody fragments which retain their specific binding sites is to be found in Winter & Milstein (1991) *Nature* 349, 293-299.

By "ScFv molecules" we mean molecules wherein the $V_H$ and $V_L$ partner domains are linked via a flexible oligopeptide.

Fab, Fv, ScFv and dAb antibody fragments can all be expressed in and secreted from *E. coli*, thus allowing the facile production of large amounts of the said fragments.

Whole antibodies, and F(ab')$_2$ fragments are "bivalent". By "bivalent" we mean that the said antibodies and F(ab')$_2$ fragments have two antigen combining sites. In contrast, Fab, Fv, ScFv and dAb fragments are monovalent, having only one antigen combining sites.

Synthetic antibodies which bind to PODXL may also be made using phage display technology as is well known in the art.

Particularly preferred anti-PODXL antibodies for use in the methods and kits of the invention are described in more detail below.

Typically, in a method of identifying the undifferentiated human embryonic stem cell, the binding moiety is detectably labelled or, at least, capable of detection. For example, the binding moiety is labelled with a radioactive atom or a coloured molecule or a fluorescent molecule or a molecule which can be readily detected in any other way. The binding moiety may be directly labelled with a detectable label or it may be indirectly labelled. For example, the binding moiety may be an unlabelled antibody which can be detected by another antibody which is itself labelled. Alternatively, the second antibody may have bound to it biotin and binding of labelled streptavidin to the biotin is used to indirectly label the first antibody.

In a preferred embodiment, the invention includes a method of identifying an undifferentiated human embryonic stem cell in a sample which may contain such cells, the method comprising contacting the sample with a binding moiety (such as an antibody) which binds to PODXL on the surface of the said cell, allowing the binding moiety (eg antibody) to bind to PODXL on the surface of the cell and determining which cells have the binding moiety (eg antibody) bound thereto.

Typically, in a method of isolating the undifferentiated human embryonic stem cells, the binding moiety is immobilised on a solid support so that the human embryonic stem cells can be isolated by affinity binding. Conveniently, the solid support comprises any suitable matrix such as agarose, acrylamide, Sepharose (a trademark) and Sephadex (a trademark). The solid support may also be a solid substrate such as a microtitre plate or the like.

Advantageously, the binding moiety is magnetically labelled (either directly or indirectly) such that, when bound, the human embryonic stem cell can be separated from the rest of the sample upon provision of a suitable magnetic field. Microbeads used for magnetic cell sorting are often termed MACS colloidal super paramagnetic microbeads.

The human embryonic stem cells labelled in this way may be sorted by magnetic activated cell sorting (MACS).

Suitably, the binding moiety is labelled with a fluorescent molecule (either directly or indirectly) and the human embryonic stem cells are isolated using a fluorescence activated cell sorter (FACS).

In a preferred embodiment, the invention includes a method of isolating an undifferentiated human embryonic stem cell from a sample containing such cells, the method comprising the steps of contacting the sample with a binding moiety (such as an antibody) which binds to PODXL on the surface of the said cell, allowing the binding moiety (eg antibody) to bind to PODXL on the surface of the cell, separating the binding moiety-cell complex from the remainder of the sample and, optionally, releasing the cell from the binding moiety.

In a particularly preferred embodiment of the fourth aspect of the invention, the said undifferentiated human embryonic stem cell is destroyed by virtue of being bound to a binding moiety which binds to PODXL. Conveniently, the binding moiety is an antibody.

The antibody may itself lead to killing of the undifferentiated human embryonic stem cells. For example, the binding of the antibody to PODXL on the cell surface may lead to an increase in cell permeability (as evidenced hypermeability to dyes such as propidium iodide/trypan blue) and cell shrinkage. Alternatively, the antibody (or other binding moiety) may further be linked to a cytotoxic moiety which can destroy the said cell when the linked antibody is bound to the cell.

Suitable cytotoxic moieties, which can be linked to an antibody or other binding moiety, include radioactive atoms, cytotoxic drugs, cytotoxic proteins and enzyme systems that convert a prodrug into a cytotoxic drug. These are well known in the art.

In a preferred embodiment, the invention includes a method of destroying an undifferentiated human embryonic stem cell in a sample containing such cells, the method comprising the steps of contacting the sample with a binding moiety (such as an antibody) which is toxic to the said cell, and allowing the binding moiety (eg antibody) to bind to the PODXL on the surface of the said cell and allowing the binding moiety kill the said cell. The binding moiety may be an antibody which itself is cytotoxic to the said cell or may include a further moiety which is toxic to the cell.

It will be appreciated from the foregoing that the invention also includes use of a moiety which binds PODXL for identifying an undifferentiated human embryonic stem cell in a sample containing such cells; use of a moiety which binds PODXL for isolating an undifferentiated human embryonic stem cell from a sample which containing such cells; use of a moiety which binds to PODXL for removing an undifferentiated human embryonic stem cell from a sample which containing such cells; use of a moiety which binds to PODXL for destroying undifferentiated human embryonic stem cells in a sample which containing such cells.

Preferably, the binding moiety is an antibody.

The invention also provides a moiety which binds to PODXL further comprising a detectable label. The invention also provides a moiety which binds to PODXL further comprising a cytotoxic moiety. Preferably, the binding moiety is an antibody.

A further aspect of the invention provides a kit of parts comprising a moiety which binds PODXL and a further agent that detects another human embryonic stem cell marker. Preferably, the other human embryonic stem cell marker is any of Oct4, SSEA-4, Tra-1-60, Tra-1-81 and GCTM-2. Still preferably, the other human embryonic stem cell marker further includes any of mAb 5, mAb 8, mAb 14, mAb 63, mAb 84, mAb 85, mAb 95, mAb 375, mAb 432 and mAb 529.

Typically, the kit comprises an antibody to PODXL and an antibody to one or more of Oct4, SSEA-4, Tra-1-60, Tra-1-81 and GCTM-2. Typically, the kit may also contain reagents for use in immunochemistry; the antibodies immobilised to a support; means for labelling the antibodies; means for linking the antibodies to a cytotoxic moiety.

It will be appreciated that for all embodiments of the invention it is preferred that the antibodies are selective. Thus, it is preferred that the antibody to PODXL selectively binds PODXL ie binds PODXL with a greater affinity than other human proteins. Typically, the anti-PODXL antibody binds substantially no other human proteins. Further anti-PODXL antibodies useful in the practice of the invention are described below in more detail.

The invention also provides an undifferentiated human embryonic stem cell (or a composition enriched for such cells) isolated by the method of the second aspect of the invention. The invention also includes an isolated undifferentiated human embryonic stem cell which cell expresses PODXL on its surface. Typically, the isolated human embryonic stem cell, or compositions enriched for the human embryonic stem cell, are provided as pharmaceutical compositions.

Thus, the invention includes a method of producing a pharmaceutical composition of human embryonic stem cells by carrying out the method of the second aspect of the invention and preparing them into a pharmaceutical composition, for example by using suitable sterile and pyrogen-free reagents.

The isolated or enriched undifferentiated human embryonic stem cells may be used to treat a patient in need of cell therapy. An effective amount of the cells may be administered to the patient, typically under the supervision of a medical practitioner.

The invention also provides a composition containing differentiated cells (which have been made by promoting the differentiation of undifferentiated human embryonic stem cells) but which is depleted of undifferentiated human embryonic stem cells using the method of the third or fourth aspect of the invention. The invention also provides a composition containing cells differentiated from undifferentiated human embryonic stem cells which composition contains substantially no undifferentiated human embryonic stem cells which express PODXL on their surface.

These compositions are typically provided as pharmaceutical compositions. Thus, the invention includes a method of making a pharmaceutical composition by providing a composition containing differentiated cells (but depleted of undifferentiated human embryonic stem cells) as described above and preparing it into a pharmaceutical composition.

The compositions containing differentiated cells but depleted of undifferentiated human embryonic stem cells (and preferably free of such cells) are useful for treating a patient in need of cell therapy. An effective amount of the composition may be administered to the patient, typically under the supervision of a medical practitioner.

Suitable conditions for treatment with the cells or compositions include Parkinson's and Alzheimer's diseases, spinal cord injury, stroke, burns, heart disease, osteoarthritis and rheumatoid arthritis.

The amino acid sequence (and encoding polynucleotide sequence) of the $V_H$ and $V^L$ chains of mAb 84 have been determined as shown in FIGS. 11 and 12.

Thus, a further aspect of the invention provides an anti-PODXL antibody that contains the amino acid sequences i) to iii), or the amino acid sequences iv) to vi), or preferably the amino acid sequences i) to vi):

```
                                              (SEQ ID NO: 2)
    i)         SASSSVNYMY (SEQ ID NO: 3)
    ii)        DTSNLAS (SEQ ID NO: 4)
    iii)       QQWSSYPYT (SEQ ID NO: 5)
    iv)        NYWMN (SEQ ID NO: 6)
    v)         EIRLKSNNYATHYAESVKG (SEQ ID NO: 7)
    vi)        ERA
``` or a variant thereof in which one or two or three amino acids in one or more of the sequences (i) to (vi) are replaced with another amino acid.

Preferably, the antibody contains the particular amino acid sequences given. Typically, if there is variation in the amino acid sequences given, it is one or two amino acid substitutions in one or two or three or four of the sequences (i) to (vi). Typically, a variant has one or two amino acid substitutions in one or two of the sequences (i) to (vi). Conveniently, there is one amino acid substitution in one or two of the amino acid sequences (i) to (vi). In any event the antibody retains the ability to bind PODXL.

Preferably, the antibody selectively binds to the extracellular region of PODXL, and the selective binding to PODXL is conferred by the presence of these amino acid sequences.

Preferably, the antibody has at least one light chain variable region incorporating the following CDRs:

```
                                              (SEQ ID NO: 2)
         CDR1:  SASSSVNYMY (SEQ ID NO: 3)
         CDR2:  DTSNLAS (SEQ ID NO: 4)
         CDR3:  QQWSSYPYT
```

More preferably, the antibody has at least one light chain variable region comprising the amino acid sequence shown in FIG. 11 (SEQ ID NO: 8).

Preferably, the antibody has at least one heavy chain variable region incorporating the following CDRs:

```
                                              (SEQ ID NO: 5)
         CDR1:  NYWMN (SEQ ID NO: 6)
         CDR2:  EIRLKSNNYATHYAESVKG (SEQ ID NO: 7)
         CDR3:  ERA
```

More preferably, the antibody has at least one heavy chain variable region comprising the amino acid sequence as shown in FIG. 12 (SEQ ID NO: 10).

Yet more preferably, the antibody has at least one light chain variable region as defined above as defined above and at least one heavy chain variable region as defined above.

Most preferably, the antibody has at least one light chain variable region comprising the amino acid sequence as shown in FIG. 11 (SEQ ID NO: 8) and at least one heavy chain variable region comprising the amino acid sequence as shown in FIG. 12 (SEQ ID NO: 10).

However, it is appreciated that the light and heavy chain CDRs 1-3 of mAb 84 listed above may also be particularly useful in conjunction with framework regions other than those shown in FIGS. 11 and 12. Accordingly, in an embodiment, light or heavy chains having CDRs 1-3 of mAb 84 listed above may possess an alternative framework region. Suitable framework regions are well known in the art and are described for example in M. Lefranc & G. Lefranc (2001) "The Immunoglobulin FactsBook", Academic Press, incorporated herein by reference.

The antibody may be detectably labelled or it may be labelled with a cytotoxic moiety as described above. The antibody may be used in any of the methods of the first, second, third or fourth aspects of the invention, and it may be used in the kit of parts.

It will be appreciated that the CDR sequences may be used in the generation of synthetic antibodies and antibody fragments as discussed above.

A further aspect of the invention provides a polynucleotide encoding the above-mentioned antibody or a molecule containing one or both of the $V_L$ or $V_H$ chains of such an antibody. Polynucleotides encoding the $V_L$ and $V_H$ chains of mAb 84, respectively, are shown in FIG. 11 (SEQ ID NO: 9) and FIG. 12 (SEQ ID NO: 11).

The invention includes a host cell which contains one or more polynucleotides required to express the antibody. Typically, the host cell is a bacterial, yeast or mammalian cell. Chinese hamster ovary (CHO) cells are particularly suited to antibody production.

BRIEF DESCRIPTION OF THE DRAWINGS

The invention will now be described with reference to the following Figures and Example wherein:

FIG. 9. Identification of PODXL as the mAb 84 target antigen on hESC. (A) Western blot analysis of target antigen immunoprecipitated by mAb 84. Target antigen affinity purified from hESC lysate using PhyTip columns containing mAb 84 was resolved on SDS-PAGE, subjected to Western blot and probed with mAb 84 (Lane 1), mAb to human PODXL (Lane 2) and pAb to human PODXL (Lane 3). (B) Identification of PODXL by LC-MS/MS. Amino acid sequence of human PODXL (SEQ ID NO: 1) obtained from protein database search and the 6 tryptic peptides from MS analysis corresponding to PODXL (underlined and bold).

FIG. 11. Amino acid sequence (and nucleotide sequence) of the $V_L$ chain of mAb 84. The amino acids not underlined correspond to the framework region. The amino acids underlined correspond to the complementarity determining regions (CDRs). The amino acid sequence is SEQ ID NO: 8 and the nucleotide sequence is SEQ ID NO: 9.

FIG. 12. Amino acid sequence (and nucleotide sequence) of the $V_H$ chain of mAb 84. The amino acids not underlined correspond to the framework region. The amino acids underlined correspond to the CDRs. The amino acid sequence is SEQ ID NO: 10 and the nucleotide sequence is SEQ ID NO: 11.

EXAMPLE 1

Figure 1:
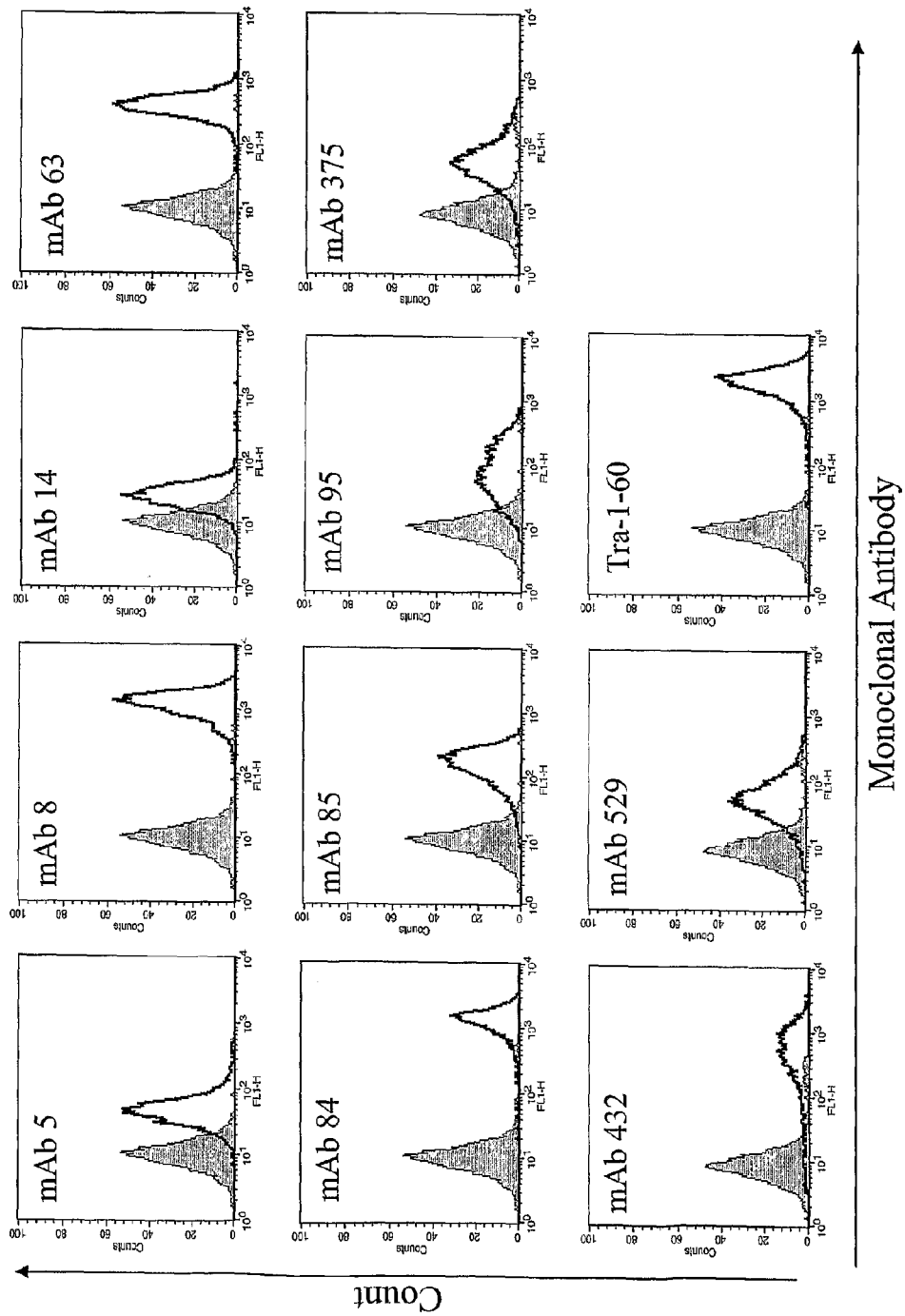
FIG. 1. Flow cytometric analysis of mAb binding to undifferentiated hESC lines. Single cell suspensions of HES-3 cells were stained with different mAb clones raised against cell surface antigens on hESC or mAb to Tra-1-60. Antibodies bound to cells were detected with a FITC-conjugated anti-mouse antibody. The shaded histogram represents staining with the negative control and open histograms represent staining with primary antibodies.

Monoclonal Antibody Targeting Podocalyxin-Like Protein Binds and Kills Undifferentiated Human Embryonic Stem Cells Introduction Human embryonic stem cells (hESC), derived from the inner cell mass of blastocysts, are pluripotent stem cells that have the ability to proliferate indefinitely in vitro in the undifferentiated state. Under the appropriate conditions, hESC can also be differentiated in vitro and in vivo to cell types representative of all three germ layers (mesoderm, endoderm and ectoderm). Morphologically, the cells have a high nuclear to cytoplasmic ratio and grow as distinct colonies. They also express high levels of alkaline phosphatase, telomerase and the transcription factors Oct-4 and Nanog [1-4]. Routinely, hESC are characterized by the expression of cell surface markers, including stage-specific embryonic antigens (SSEA)-3 and SSEA-4, tumor rejection antigen (Tra)-1-60 and Tra-1-81. However, these surface antigens are not unique to hESC and have been previously characterized in human embryonal carcinoma (EC) cells [5,6]. Furthermore, the monoclonal antibodies (mAbs) targeting these antigens were raised against human EC cells and mouse embryos.

To date, only Son and colleagues have described the use of hESC as an immunogen to generate mAbs to cell surface markers [7]. The generation of mAbs specific to hESC surface markers is important because it allows for the identification of novel antigens whose expression is restricted to undifferentiated hESC. Elucidating the role/mechanism of these different cell surface antigens in development and pluripotency will contribute to the understanding of stem cell regulation. Another benefit for having hESC-surface specific mAbs would be the ability to incorporate them into a cell separation process before therapy. Following differentiation of hESC to cells of a specific lineage, it is crucial to eliminate residual undifferentiated hESC from the population because these cells could potentially result in the formation of teratomas in vivo after transplantation [8,9].

In this study, a panel of 10 mAbs was generated following immunization of BALB/C mice with live hESC. These mAbs showed strong reactivity to undifferentiated hESC lines, however, reactivity was reduced or absent in hESC-derived embryoid bodies, mouse embryonic stem cells, mouse feeders, human EC cells and other human cell lines. Interestingly, one of the clones, mAb 84, which reacts with podocalyxin-like protein-1 (PODXL) not only binds but also kills undifferentiated hESC within 15-30 min of incubation in a concentration-dependent and complement-independent manner. Cytotoxicity was restricted to the undifferentiated phenotype, and differentiation of hESC resulted in a reduction in killing efficiency by this mAb. Because of its selectivity to undifferentiated hESC, mAb 84 could be used to remove or kill residual hESC prior to transplantation of the differentiated cell types. To our knowledge, this is the first report of a cytotoxic mAb specifically targeting undifferentiated hESC.

Materials & Methods

Cell Culture

Human embryonic stem cell lines, HES-2 (46 X,X), HES-3 (46 X,X) and HES-4 (46 X,Y) were obtained from ES Cell International. The cells were cultured at 37° C./5% $CO_2$ either on mitomycin-C inactivated feeders (~7×10$^4$ cells/cm$^2$) in gelatin-coated organ culture dish (co-cultures) or on matrigel-coated organ culture dishes supplemented with conditioned media from immortalized mouse feeders, E-MEF (feeder-free cultures) [1]. Media used for culturing HES cells was either HES media or KNOCKOUT (KO) media. HES media contained 80% DMEM with high glucose supplemented with 20% FBS (Hyclone), 10 ml insulin-transferrin-selenium solution/L of media, 25 U/ml penicillin, 25 µg/ml streptomycin, 2 mM L-glutamine, 0.1 mM non-essential amino acids (NEAA) and 0.1 mM 2-mercaptoethanol; and KO-media contained 85% KO-DMEM supplemented with 15% KO serum replacer, 1 mM L-glutamine, 0.1 mM NEAA and 0.1 mM 2-mercaptoethanol and 4 ng/ml of basic fibroblast growth factor (Invitrogen). For co-cultures, the hESC colonies were passaged by mechanical dissection using pulled glass capillaries [2]; for feeder-free cultures, hESC were passaged following enzymatic treatment as described previously [2].

Mouse embryonic stem cell lines (mESC), CS-1 and E14 were gifts from Dr Chyuan-Sheng Lin (College of Physicians and Surgeons, Columbia University [3]) and Dr Bing Lim (Genome Institute of Singapore[4]) respectively and were cultured as described previously[5]. Human embryonal carcinoma (EC) cell line 2102 Ep was a gift from Prof Peter Andrews (University of Sheffield) and was cultured as described before [6]. Human EC and cancer cell lines NTERA-2 cL.D1 (CRL-1973), NCCIT (CRL-2073) and HeLa (CCL-2) were purchased from the American Type Culture Collection and cultured according to the ATCC instructions. Human embryonic kidney cell line, 293-HEK (Gibco-BRL, Life Technologies) was cultured according to the protocol provided. To induce embryoid bodies (EB) formation from HES-3 cells (i.e. to induce hESC differentiation from HES-3 cells in vitro), hESC were harvested as clumps and cultured as aggregates (i.e. as embryoid bodies) for 8 days in EB-medium (80% KO-DMEM, 20% FCS, 25 U/ml penicillin, 25 µg/ml streptomycin, 2 mM L-glutamine, 0.1 mM NEAA, and 0.1 mM 2-mercaptoethanol) on non-adherent suspension culture dishes (Corning). Subsequently, the EB were dissociated with trypsin and plated on gelatinized culture dishes in EB-medium for an additional 14 days [16].

Generation of Monoclonal Antibodies

Two 6-week old female Balb/C mice received 5 consecutive weekly immunizations of 5×10$^6$ HES-3 cells/mice suspended in PBS+ or MPL+TDM Adjuvant (Sigma) in the intraperitoneal cavity. Splenocytes from the mice were fused with SP2/0 mouse myeloma cells using the ClonaCell™-HY Hybridoma Cloning Kit (StemCell Technologies Inc). Briefly, a single cell suspension of splenocytes (1×10$^8$ cells) was fused with 2×10$^7$ SP2/0 cells using the supplied polyethylene glycol (PEG) and Medium B. After an overnight incubation at 37° C., hybridomas were plated using methylcellulose-based Medium D. Individual clones of hybridomas were isolated 10-14 days after plating and cultured in 96-well followed by 24-well tissue culture plates containing Medium E. Culture supernatant from each hybridoma was collected and reactivity to hESC was assessed by flow cytometry. Isotyping of the antibody was performed using the ClonalCell™-InstantCHEK Isotyping Kit (StemCell Technologies).

Flow Cytometry Analysis

Antibody reactivity with surface markers on different cell populations was assessed by immunofluorescence using flow cytometry. Cells were harvested as a single cell suspensions using trypsin, resuspended at 2×10$^5$ cells per 10 µl volume in 1% BSA/PBS and incubated for 45 min with each mAb clone (150 µl culture supernatant or 5 µg purified mAb in 200 µl 1% BSA/PBS) or mAb to SSEA-4 (neat, Developmental Studies Hybridomas Bank), Tra-1-60, Tra-1-81 (2.5 µg in 200 µl 1% BSA/PBS, Chemicon, MAB4360/4381), human-podocalyxin (PODXL, R&D systems, MAB1658) and polyclonal antibody (pAb) to human PODXL (5 µg in 200 µl 1% BSA/PBS, R&D systems). Cells were then washed with cold 1% BSA/PBS, and further incubated for 15 min with a 1:500 dilution of goat a-mouse antibody FITC-conjugated (DAKO). After incubation, the cells were again washed and resuspended in 1% BSA/PBS and 1.25 mg/ml propidium iodide (PI) for analysis on a FACScan (Becton Dickinson FACS Calibur). All incubations were performed at 4° C.

unless otherwise indicated. As a negative control, cells were stained with the appropriate isotype control.

For co-expression studies, hESC were incubated with primary antibody and washed with 1% BSA/PBS as described above. After which, cells were fixed, permeabilized (Caltag Laboratories) and incubated with a mouse mAb to Oct-4 (Santa Cruz sc-5279) at a 1:20 dilution. Cells were then washed with 1% BSA/PBS, and incubated in the dark with a 1:500 dilution of goat anti-mouse IgG (K-chain specific) antibody FITC-conjugated (Sigma) and rabbit anti-mouse IgM antibody PE-conjugated (Open Biosystems). After incubation, the cells were again washed and resuspended in 1% BSA/PBS for analysis. All incubations other than primary antibody were performed at room temperature for 15 min. As a negative control, cells were stained with the appropriate isotype control.

Immunocytochemistry

Cells were fixed in 4% paraformaldehyde at room temperature for 45 min and incubated with culture supernatant from each mAb clone at room temperature for 1 h. Localization of antibodies was visualized using goat anti-mouse antibody conjugated with either fluorescein isothiocyanate (FITC) or phycoerythrein (PE) (1:500 dilution; DAKO).

Cytotoxicity Assays

Cytotoxicity of mAb 84 on cells was evaluated using PI exclusion assays and flow cytometry. As described above, single cell suspensions at $2\times10^5$ cells per 10 μl volume in 1% BSA/PBS were incubated with mAb 84 (150 μl culture supernatant or 5 μg purified mAb in 200 μl 1% BSA/PBS), mAb to human PODXL or pAb to human PODXL (5 μg in 200 μl 1% BSA/PBS, R&D systems) at 4° C. for 45 min. After which, cells were washed and resuspended in 1% BSA/PBS and 1.25 mg/ml propidium iodide (PI) for analysis by FACS. For dosage studies, HES-3 cells were incubated with 0.1, 0.5, 1, 5 and 15 μg purified mAb 84 in 200 μl 1% BSA/PBS. For time course studies, HES-3 cells were incubated with 5 μg purified mAb 84 in 200 μl 1% BSA/PBS and harvested for analysis at 15, 30 and 45 min after addition of the mAb. For hypercrosslinking experiments, HES-3 cells after primary mAb incubation were washed and further incubated with a goat anti-mouse secondary antibody (5 μg in 200 μl 1% BSA/PBS, DAKO) for 45 min. As a negative control, cells were incubated with the isotype control mAb 85. All incubations were performed at 4° C. unless otherwise indicated. To validate the results obtained using PI exclusion assays, viability for each sample was also determined using trypan blue exclusion.

Immunoprecipitation

In order to identify the antigen target for mAb 84, feeder-free cultures of hESC were grown to confluence in 6 cm Petri dishes (Falcon), washed with PBS+ and lysed by scraping in 2% Triton/PBS+. Cell lysate was clarified by centrifugation and used immediately for immunoprecipitation (IP).

IP of the antigen was carried out using the automated MEA system (Phynexus, Inc). Briefly, mAb 84 (~100 μg) was isolated from hybridoma culture supernatant by direct capture onto Protein A PhyFip® columns (5 μl resin bed, Phynexus, Inc). After washing away unbound proteins in the supernatant with Wash Buffer I (10 mM $NaH_2PO_4$/140 mM NaCl pH 7.4) clarified cell lysate from approximately $5\times10^6$ cells was passed through the column functionalized with the captured mAb 84. The column was further washed with Wash Buffer II (140 mM NaCl pH 7.4) and bound proteins were eluted from the column at low pH with Elution Buffer (200 mM $NaH_2PO_4$/140 mM NaCl pH 2.5) and neutralized immediately with 1 M Tris-Cl pH 9.0. The eluate was stored at 4° C. for further analysis.

SDS-PAGE and Western Blot Analysis

SDS-PAGE and Western blotting were performed essentially by the methods of Laemmli [7] and Towbin [8] respectively. Briefly, eluates from IP were separated by SDS-PAGE (NuPAGE 4-12% gradient gel, Invitrogen) under reducing conditions followed by either Western Blotting or silver staining of the gel. For Western Blotting, resolved proteins were transferred electrophoretically onto PVDF membrane (Millipore) at 100 V for 2 h. The membranes were then immunoblotted with either mAb 84 culture supernatant (diluted 1:1 with 1% BSA/PBS/0.1% Tween-20), mouse mAb to human PODXL or goat pAb to human podocalyxin (200 ng/ml, R&D Systems) followed by goat anti-mouse or rabbit anti-goat antibodies HRP-conjugated (1:10000 dilution, DAKO and Pierce respectively). Binding of HRP-conjugated secondary antibodies were visualized by ECL detection (Amersham Biosciences). Silver staining was performed using SilverQuest silver staining kit (Invitrogen) according to the manufacturer's protocol and the protein band corresponding to the band on the Western Blot was manually excised.

Mass Spectrometry

Reduction, Alkylation and Proteolysis

The excised gel was soaked overnight at 4° C. in washing solution (2.5 mM ammonium bicarbonate in 50% aqueous acetonitrile) followed by an additional 20 min incubation at 37° C. after a change in washing buffer. The gel was then dried and subjected to reduction and alkylation. Briefly, 20 μl of 10 mM DTT in 100 mM ammonium bicarbonate was added to each gel spot and incubated at 56° C. for 1 h. After which, 20 μl of 55 mM iodoacetamide IAA in 100 mM ammonium bicarbonate was added and incubated at room temperature for 45 mM in the dark. The gel spot was then washed and dehydrated twice in 100 mM ammonium bicarbonate and 100% acetonitrile respectively. For proteolysis, the protein in each gel spot was digested with modified trypsin (0.02 μg/μl in 25 mM ammonium bicarbonate, Promega) at 37° C. overnight with shaking. After tryptic digestion, 1% formic acid and 2% methanol was added to the samples to a final volume of 9 μl for LC MS/MS analysis.

LC-MS/MS and Protein Identification

Digested samples were separated using a nano-flow high-performance liquid chromatography (HPLC) system (LC Packings). Each sample of 9 μl was injected and concentrated onto a trap cartridge (grecolumn, 300 um×5 mm, C18 PepMap 100, LC Packings) in 0.1% formic acid in water at a flow rate of 25 μ/min. After 5 min of washing, the flow was switched in line to a resolving column (75 um internal diameter Picotip Emitter, New Objective) with 10 cm of C18 reversed-phase packing material (Column Engineering) and the flow rate decreased to 100 nl/min. A gradient was then developed from 0 to 60% acetonitrile in 0.1% formic acid over 60 min. Using a liquid junction at the distal end of the column a voltage of 2300 v was introduced to form a spray at the tip of the column directed at the inlet orifice of a quadrupole-time of flight (Qq-tof) hybrid tandem mass spectrometer (QSTAR-XL, Applied Biosystems). The mass spectrometer was run in Information Dependent Acquisition (IDA) mode to capture and fragment doubly and triply charged mass ions automatically. Selected mass ions with a minimum signal of 8 counts/sec were isolated and fragmented with nitrogen gas. The collision energy used was proportional to the mass of the peptide and was calculated during analysis using the Analyst-QS software (Applied Biosystems). Proteins were identified by searching the MS/MS spectral files against the UniProt (EBI) protein database using the MASCOT (Matrix Science) search engine.

Results

Reactivity of mAbs with hESC and Other Cells Lines in Vitro

Figure 2:
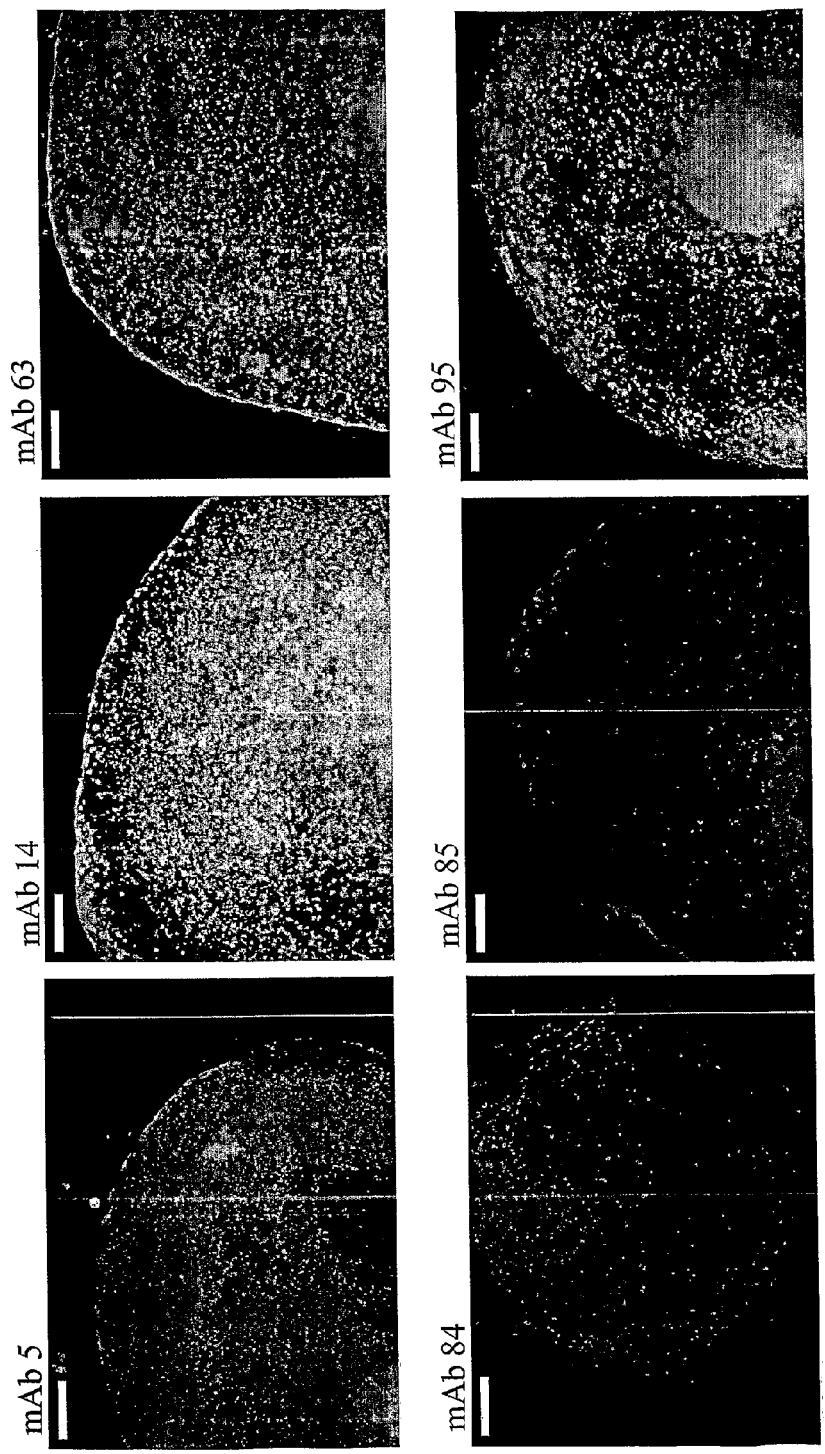
FIG. 2. Analysis of mAb binding to cell surface antigens on hESC colonies by immunocytochemistry. Immunostaining of HES-3 colonies cultured on feeders with different mAb clones raised against cell surface antigens on hESC. Colonies were subsequently stained with anti-mouse detection antibody conjugated with either FITC (mAb 5, 14, 63 and 95) or PE (mAb 84 and mAb 85). Negative staining was observed with the isotype control SSEA-1 (data not shown). Images were taken at 40× magnification and the scale bar represents 200 µm.

In order to raise a panel of mAbs to cell surface markers on undifferentiated hESC, viable HES-3 cells were used to immunize Balb/C mice either in PBS in the absence of adjuvant or in MPL+TDM adjuvant. A total of 114 hybridomas were isolated from the fusion. Following primary screening of their reactivity to HES-3 cells using flow cytometry, a panel of 10 antibodies was found to bind to hESC surface antigens (FIG. 1). Furthermore, binding of the mAbs to HES-3 colonies was confirmed by immunocytochemistry (FIG. 2). By isotyping, it was found that 9 of the mAbs are IgMs whilst the remaining one is $IgG_{2a}$ (mAb 8). Screening with other hESC lines, HES-2 and HES-4 revealed that the reactivity was not only limited to the immunogen, HES-3 (Table 1). Furthermore, antibody binding was reduced after the cells were induced to form embryoid bodies (EBs) suggesting a down-regulation of antigen expression during differentiation.

Secondary screening was performed for these 10 clones to determine the cross reactivity of the mAbs with other cell lines, namely mouse feeders (E-MEF), mouse embryonic stem cells (mESC), human embryonic carcinoma cell (EC) and miscellaneous human cell lines (HEK-293, HeLa) (Table I). It was observed that there was no reactivity of the mAbs with the mouse feeders which the hESC were cultured on prior to immunization. In addition, mAb reactivity (i.e. target antigen expression) was restricted to hESC cells and not to the 2 mESC lines tested (except mAb 14 on CS-1). When we compared the reactivity of Tra-1-60, Tra-1-81 and SSEA-4 with our panel of mAbs on human EC cells, as expected, strong reactivity was observed for all 3 antibodies (Tra-1-60/81 and SSEA-4) on the EC lines tested. In contrast, most of our mAb panel had weak reactivity with at least 2 of the three EC lines. Interestingly, mAbs 84, 95, 375, 432 and 529 had no or weak reactivity with NTERA, 2102 Ep or NCCIT. This result is indicative that there are differences in antigen profile/expression between hESC and EC; and even between different EC cell lines. Furthermore, when screened against other human cell lines, 7 of the mAb clones (including mAb 84, 95, 14 and 85) do not bind to HEK-293 or HeLa cells. However, for mAb 5 and mAb 63, the reactivity with these 2 cell lines increased compared to hESC implying the up-regulation of antigen expression as the cells terminally differentiate.

Figure 3:
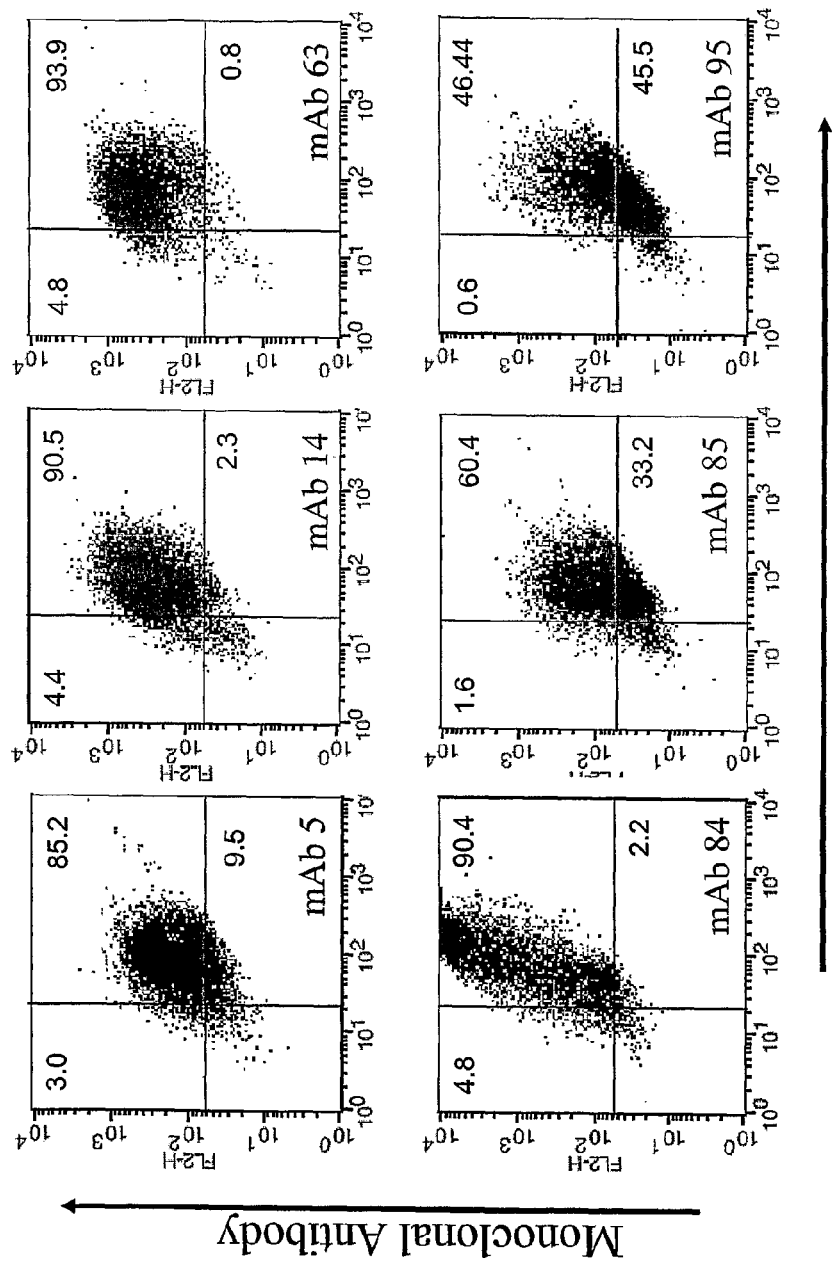
FIG. 3. Two-colour flow cytometric analysis of HES-3 cells stained with various hESC-binding mAbs and mAb to Oct-4. Single cell suspensions of hESC were sequentially stained with different hESC-binding mAb clones followed by mAb to Oct4. Antibodies bound to cells were detected simultaneously with anti-mouse IgG specific antibody FITC-conjugated and anti-mouse IgM antibody PE-conjugated. The marker for the plot was positioned to represent the fluorescence of >95% of the appropriate FITC- or PE-conjugated isotype control in the lower left quadrant.

To further characterize the mAb panel, we compared the co-expression of the hESC pluripotent marker Oct-4 with the antigens targeted by the IgM mAb in the panel. FIG. 3 shows 2-colour flow cytometric analysis of the HES-3 cell line. From the scatter plots, >95% of mAb-positive HES-3 cells are positive for Oct-4 suggesting a strong correlation between target antigen expression and Oct-4 expression.

Characterization of the Cytotoxic Antibody mAb 84

Figure 4:
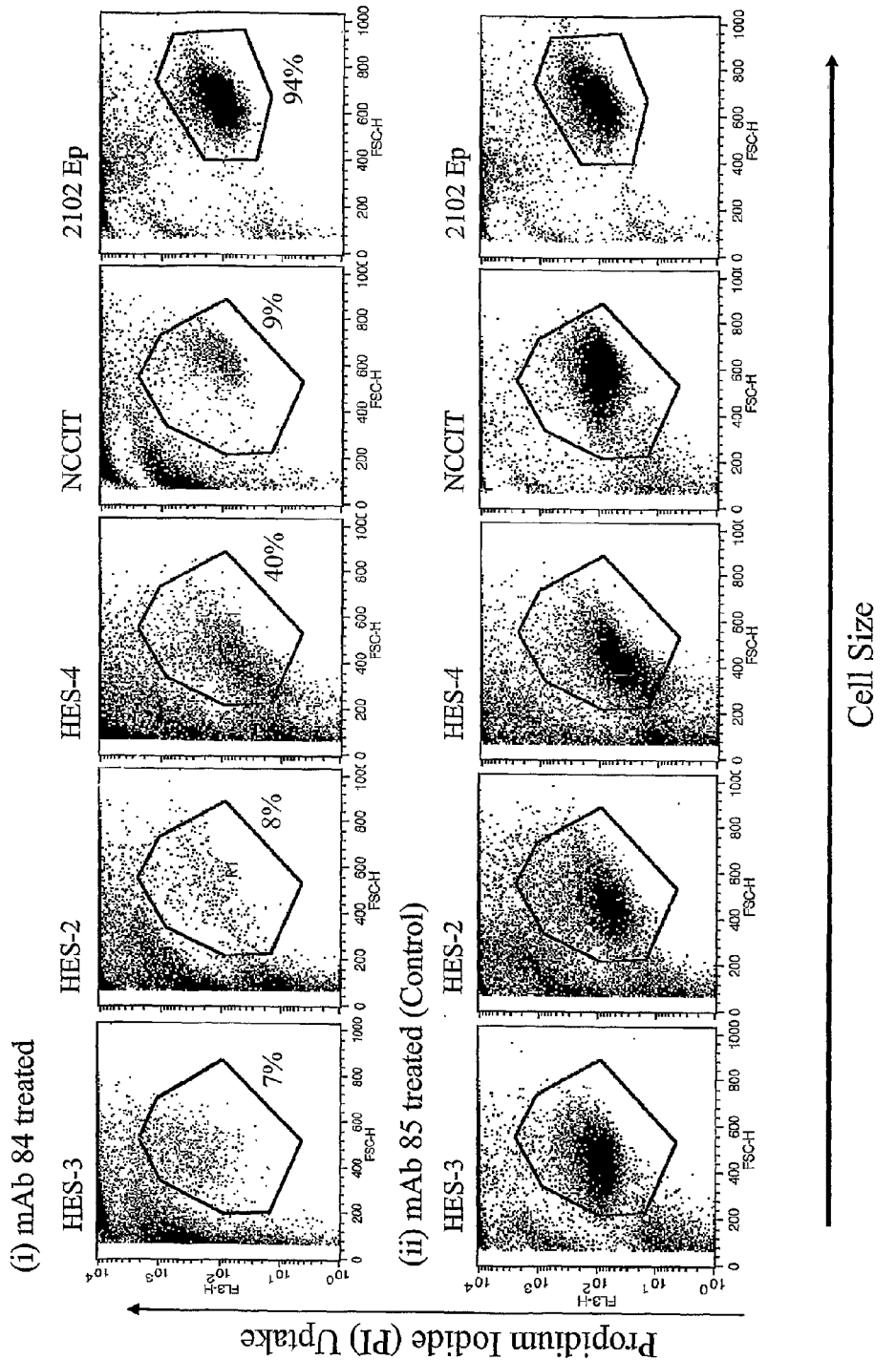
FIG. 4. Cytotoxic effect of mAb 84 on hESC and EC cells. Cell suspensions (2×10⁵) were incubated with 5 µg mAb 84 or mAb 85 (Isotype control) at 4° C. for 45 min. After which, cells were harvested for analysis by PI exclusion assay on the flow cytometer. Gated region in the scatter plot represents the viable cell population.
Figure 5:
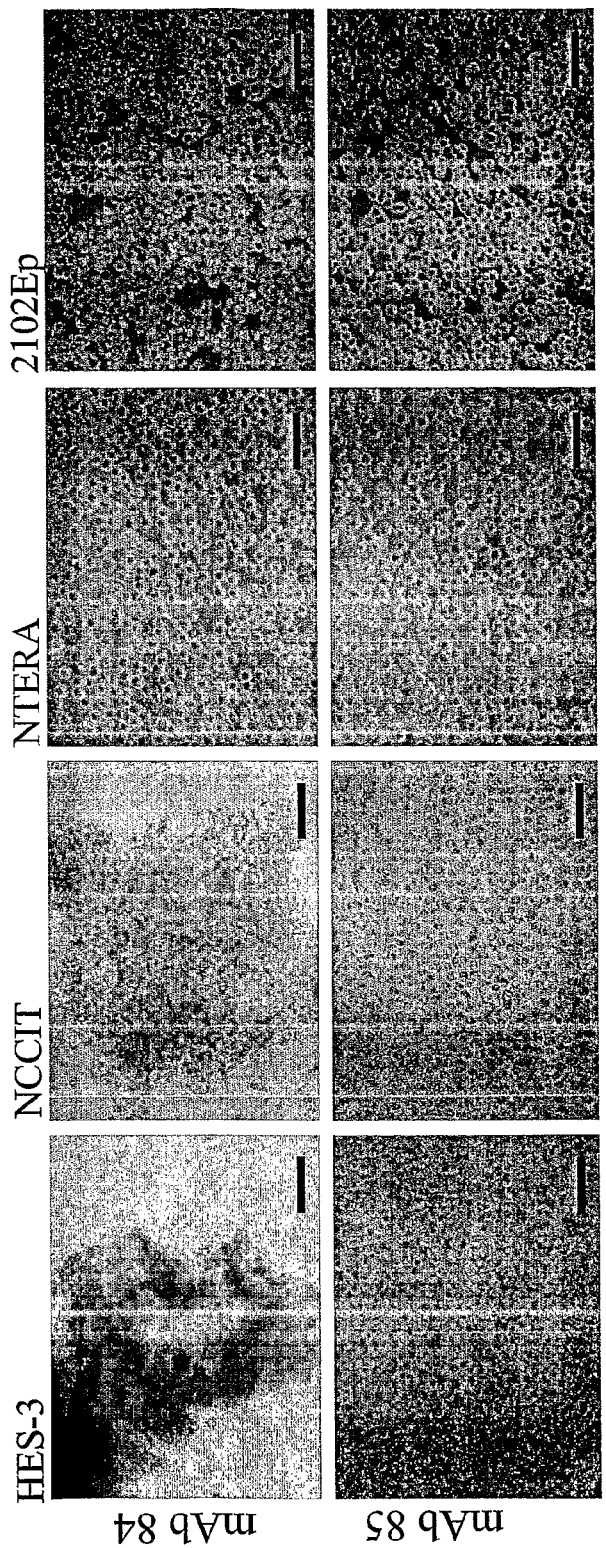
FIG. 5. Microscopic analysis of hESC and EC cells incubated with mAb 84. Single cells suspensions (2×10⁵) were incubated with 5 µg mAb 84 or mAb 85 (Isotype control) at 4° C. for 45 min in 24-well plates and analyzed microscopically. Images were taken at 100× magnification and the scale bar represents 100 µm.

During screening of the antibody panel, it was found that HES-3 cells incubated with mAb 84 had a significant decrease in viability compared to cells incubated with other IgM mAbs (e.g. mAb 85) (FIG. 4, column 1). Based on PI exclusion assays, only 7% of cells remained viable after the incubation period with mAb 84 (45 min at 4° C.) compared to mAb 85. This cytotoxic effect of mAb 84 on hESC was also observed on 2 other hESC cell lines, HES-2 and HES-4 and the EC line, NCCIT (FIG. 4, columns 2-4) with a viability of 8%, 40% and 9% respectively after incubation with mAb 84. In contrast, another EC line, 2102 Ep, maintained a viability of 94% after incubation (FIG. 4, column 5). When the cells were visualized under phase contrast microscopy, it was apparent that HES-3 and NCCIT cells incubated with mAb 84 showed significant clumping compared to NTERA and 2102 Ep cells incubated with mAb 84 or to HES-3 and NCCIT cells incubated with mAb 85 (FIG. 5). Based on these binding and cytotoxicity data, it can be interpreted that the cytotoxic effect on mAb 84 is dependent on the binding of the mAb with the cell line (Table I). The mAb do not exert a cytotoxic effect on cells that do not bind the mAb.

Figure 6:
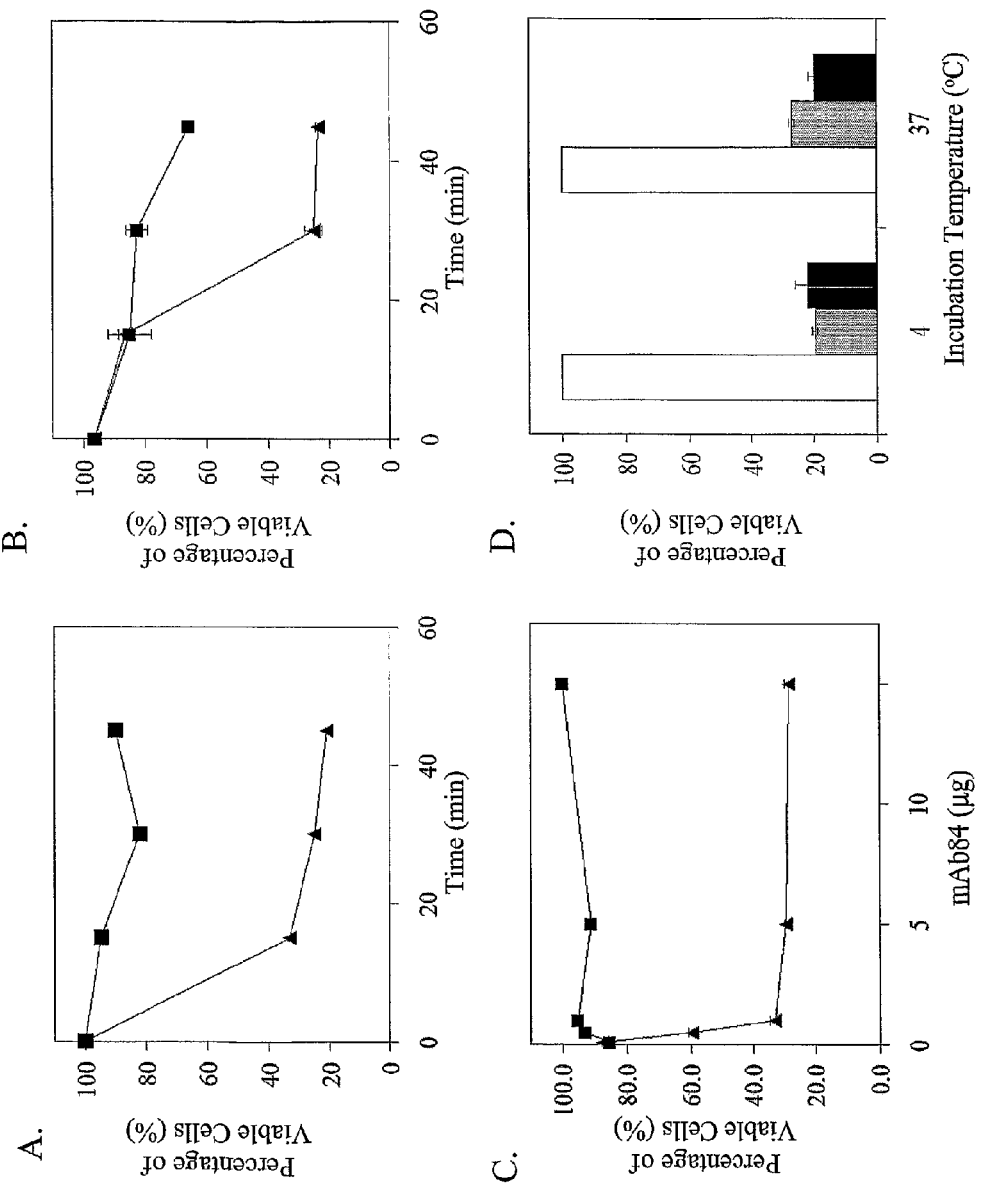
FIG. 6. Characterization of mAb 84-mediated killing of hESC (A and B) Time course study. HES-3 cells were incubated with 5 µg of mAb 84 (▲) and mAb 85 (■, Isotype control) at 4° C. Cells were harvested at 15, 30 and 45 min after the addition of the mAb and cell viability was analyzed by PI exclusion or trypan blue exclusion assays. (C) Effect of mAb 84 dosage on hESC killing. HES-3 cells (2×10⁵) were incubated with 0.1-15 µg of mAb 84(▲) and mAb 85 (■) at 4° C. After 45 min, cells were harvested and viability was assessed by PI exclusion assay. (D): HES-3 cells were incubated with purified (▨) and non-purified (culture supernatant) (■) mAb 84 at 4° C. and 37° C. for 45 min. The cells were then harvested for analysis by PI exclusion assay on the flow cytometer. Incubation with mAb 85 served as an isotype control (□).

In time course studies, HES-3 cells were incubated with 5 μg mAb 84 or mAb 85 and the cells were harvested every 15 min for analysis by PI exclusion and trypan blue exclusion assays (FIGS. 6A and B). In the PI exclusion assay, the cytotoxic effect of mAb 84 a on HES-3 cells was observed as rapidly as 15 min after incubation with the mAb, with the viability dropping to 33%. Further incubation for up to 45 min resulted in a further decrease to 20% viability. These results were confirmed by trypan blue exclusion. Interestingly, the decrease in viability based on this assay occurred between 15-30 min after incubation, however the final viability after the incubation period of 45 min also corresponded to ~20%. When the concentration of mAb 84 was titrated over the range of 0.1-15 μg, it was found that the cytotoxic effect of mAb 84 on HES-3 cells was dose dependent (FIG. 6C). Approximately 1 μg (1 pmol) of purified mAb 84 was able to cause a decrease in hESC viability to <30% (i.e. a 70% decrease in viability).

Figure 7:
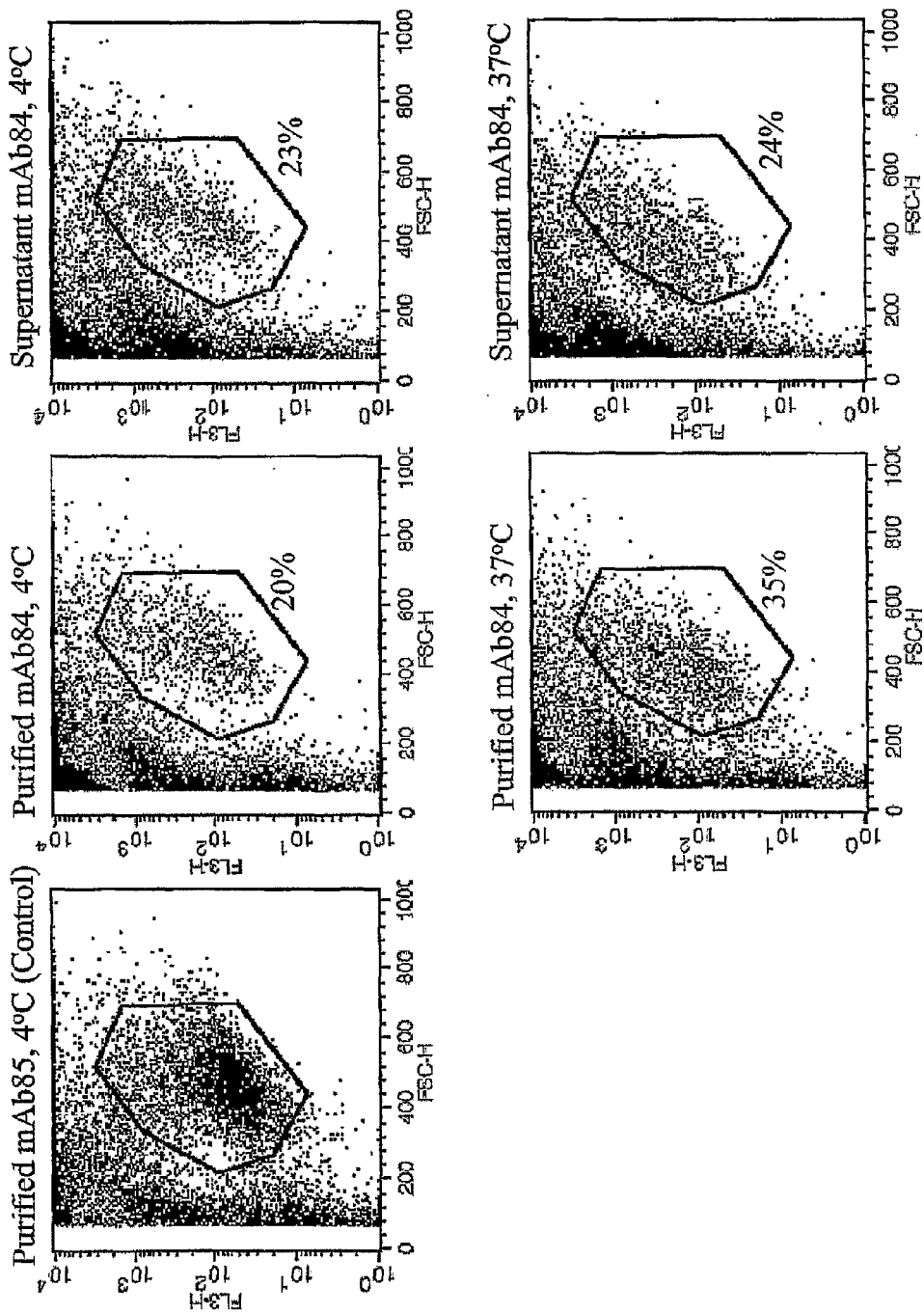
FIG. 7. Effect of temperature on mAb 84-mediated killing of hESC. HES-3 cells were incubated with purified mAb 84 or mAb 84 culture supernatant at 4° C. and 37° C. for 45 min. The cells were then harvested for analysis by PI exclusion assay on the flow cytometer. Gated region in the scatter plot represents the viable cell population. Incubation with mAb 85 served as an isotype control.

Until this stage, cytotoxicity assays had been performed at 4° C. to minimize the effect of internalization of the antigen-antibody complex into the cells. To investigate the effect of temperature on cytotoxicity, hESC was incubated with both purified and non-purified (culture supernatant) mAb 84 at 4° C. and 37° C. (FIG. 6D). By PI exclusion assays, it was found that temperature did not affect the cytotoxicity of mAb on hESC (>75% killing with non-purified mAb 84). In addition, FIG. 7 demonstrated that mAb 84 was also cytotoxic to hESC at 37° C. From the scatter plot, it was observed that there was no difference in mAb 84-mediated killing of HES-3 cells at 4° C. and 37° C. for both purified mAb 84 and mAb 84 culture supernatant.

Figure 8:
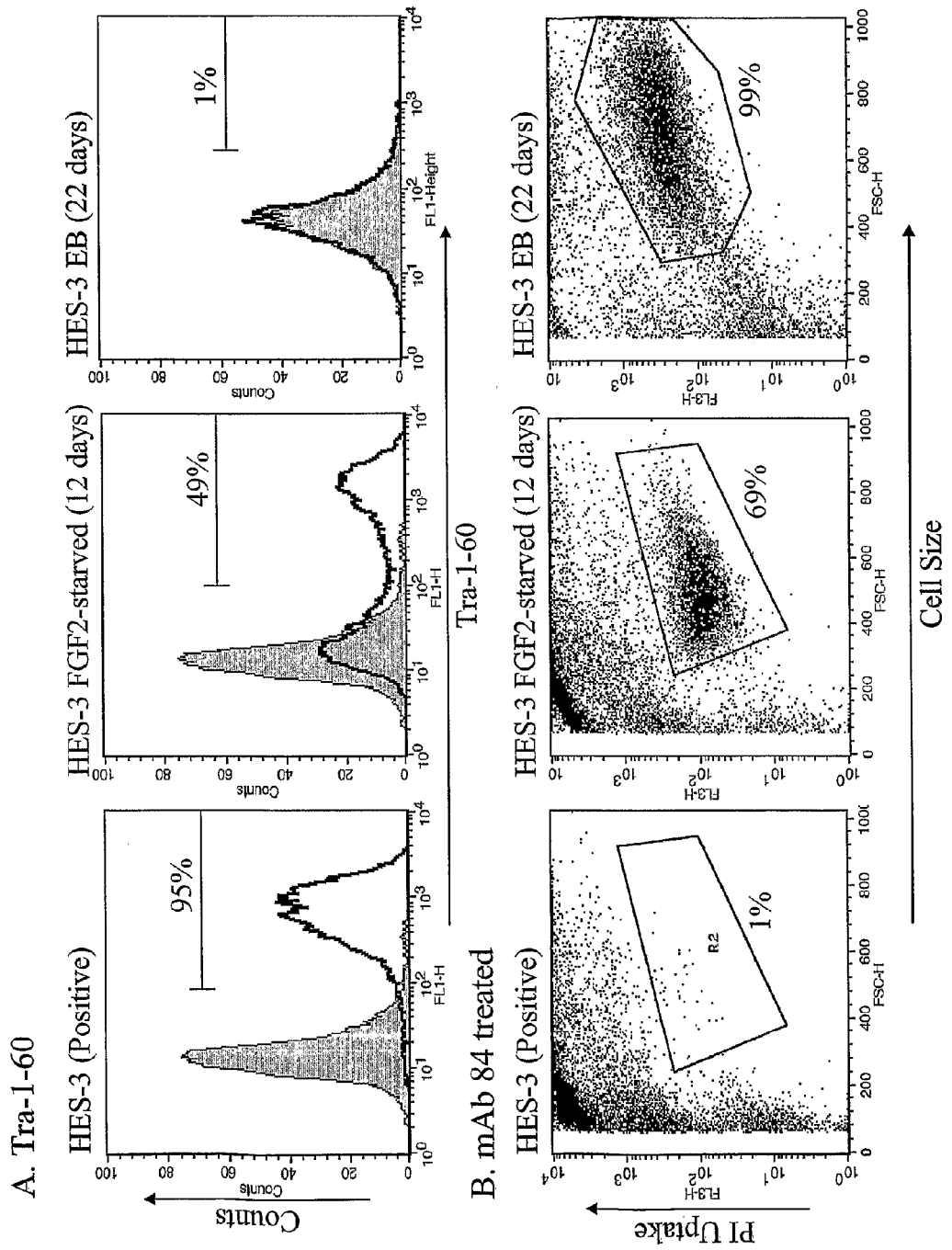
FIG. 8. Relationship between hESC pluripotency and killing efficiency by mAb 84. Single cell suspensions of undifferentiated and differentiated HES-3 cells were: (A): stained with mAb to Tra-1-60. Antibodies bound to cells were detected with a FITC-conjugated anti-mouse antibody. The shaded histogram represents staining with the negative control and open histograms represent staining with anti-Tra-1-60 mAb; (B): incubated with 5 µg mAb 84 at 4° C. for 45 min. After which, cells were harvested for analysis by PI exclusion assay on the flow cytometer. Gated region in the scatter plot represents the viable cell population.

Furthermore, mAb 84 was equally cytotoxic to hESC after purification by protein A (>77% killing was observed for both purified and non-purified mAb 84 at 4° C. incubation). This result suggests that mAb 84-induced toxicity on hESC was not complement-mediated because cell killing efficiency was comparable in the presence or absence of fetal bovine serum in the medium. We had previously observed that mAb 84 binding to hESC was down-regulated in 8 day old embryoid bodies (Table 1). In order to determine if cytotoxicity of mAb 84 was specific to the undifferentiated phenotype, hESC was induced to differentiate either by depriving the cultures of FGF2 or by EB formation (FIG. 8A). Differentiation was assessed based on the expression of the pluripotent marker, Tra-1-60. After 12 days of FGF2 withdrawal, partial differentiation of hESC was observed, with only 49% of the cell population still expressing Tra-1-60 compared to the undifferentiated hESC culture (>95% Tra-1-60 +ve). Differentiation via the EB route yielded >99% of Tra-1-60 −ve cells. When cells from these 3 conditions were incubated with mAb 84, the efficiency of cell killing corresponded closely with the percentage of Tra-1-60 +ve cells (FIG. 8B). For undifferentiated hESC, only ~1% of cells remained viable after incubation with mAb 84. This percentage increased to 69% and 99% for FGF2-starved and EB cultures respectively.

Identification and Validation of mAb 84 Antigen Target on hESC

To identify the target antigen on hESC responsible for the cytotoxic effect of mAb 84, immunoprecipitation experiments were performed. Whole cell lysate was passed through a PhyTip column containing protein A resin and mAb 84. Proteins that were captured by affinity interaction were resolved on protein gels and probed with mAb 84. Based on molecular weight markers, an antigen band of <190 kDa was detected (FIG. 9A lane 1). The lower band at ~25 kDa detected by the secondary antibody has been identified as the light chain of mAb 84 after reduction. The corresponding band on a silver-stained gel was isolated and identified by mass spectrometry. From a protein database search with the peptides obtained, the antigen band was identified as podocalyxin-like protein 1 precursor (PCLP1 or PODXL; Accession No O000592). The amino acid sequence of PODXL and the corresponding peptide matches are shown in FIG. 9B. In order to validate that the antigen target is PODXL, immunoprecipitation with mAb 84 was repeated and the eluate from the column was probed with commercially-available antibodies to PODXL (FIG. 9A lanes 2 and 3). From the Western blots, a band of comparable molecular weight was detected in all 3 lanes thus confirming the identity of PODXL. By RT-PCR, the 2 variants of PODXL (Accession Nos: NP_001018121 and O000592 for variant 1 and 2 respectively) were also found to be transcribed in hESC (data not shown).

Figure 10A:
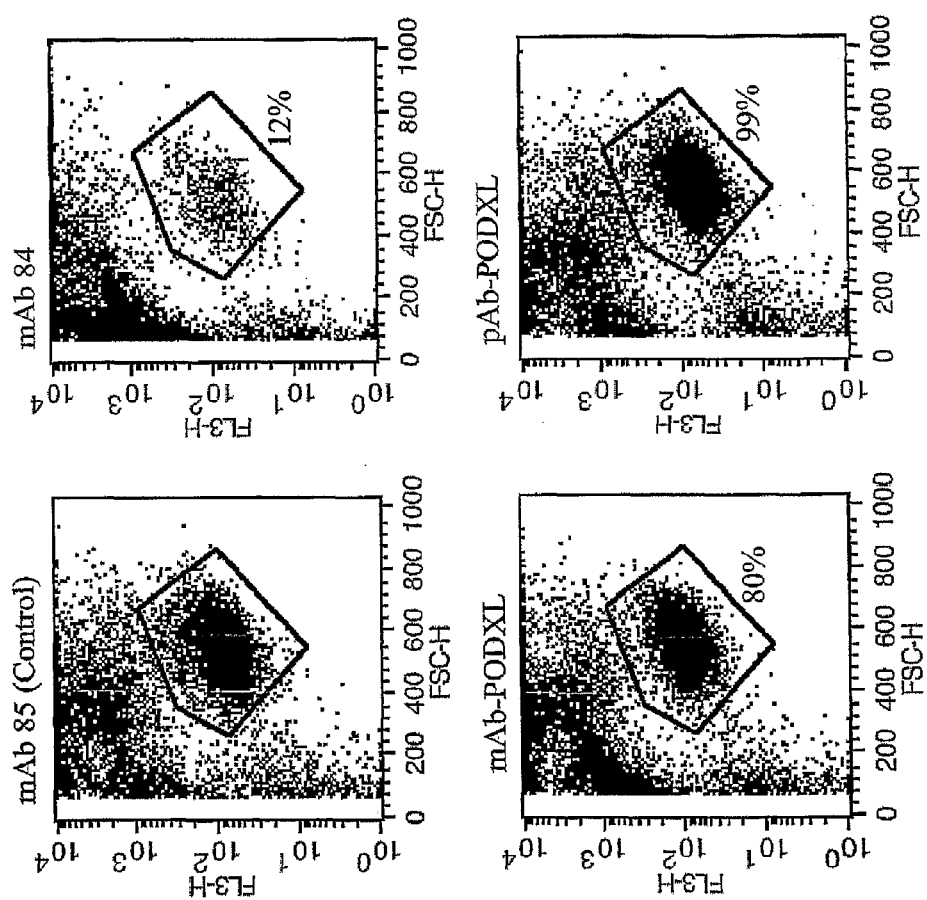
FIG. 10. Cytotoxicity of commercially-available anti-PODXL antibodies on hESC compared to mAb 84. HES-3 cells were incubated with 5 µg of mAb 84, mAb-PODXL pAb-PODXL or mAb 85 (Isotype control) at 4° C. for 45 min. In some experiments, hESC were further hypercross-linked with goat-anti mouse (GAM) antibodies. After which, cells were harvested for analysis by PI exclusion assay on the flow cytometer. Gated region in the scatter plot represents the viable cell population (A). The results are also presented in tabular form (B).
Figure 10B:
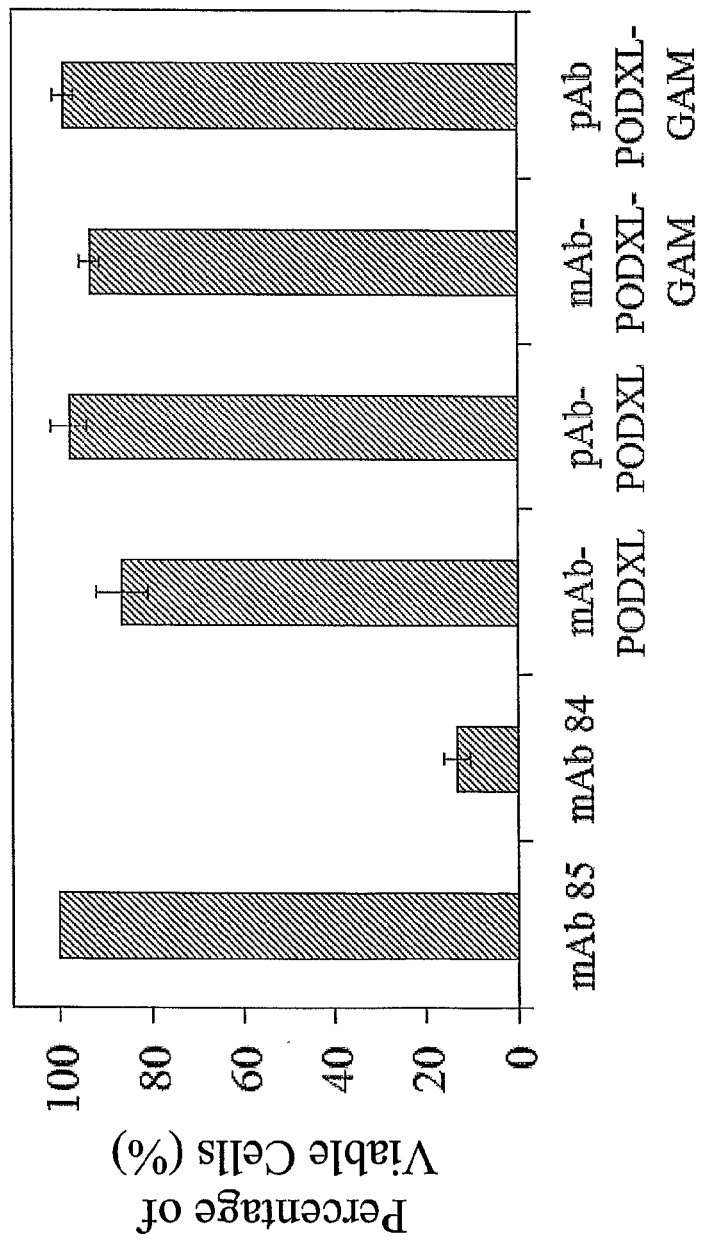

Having identified the antigen target of mAb 84, we proceeded with investigating whether commercially-available antibodies to PODXL exerted a similar cytotoxic effect on hESC. From FIGS. 10A and B, it is apparent that though the 3 sources of antibodies (mAb and pAb) were specific to human PODXL, cytotoxicity was only observed for mAb 84 and not for the 2 commercially available sources of anti-PODXL antibodies. It has been previously reported that apoptosis can be induced by hypercross-linking of primary antibodies bound to antigens on cells, such as CD19, 20 and 22 on cells [19,20]. Since mAb 84 is an IgM (pentameric) whilst mAb-PODXL and pAb-PODXL are both IgG (bivalent), we investigated whether hypercross-linking of mAb-PODXL or pAb-PODXL with goat-anti mouse (GAM) antibodies would mimic mAb 84-mediated killing of hESC. Incubation of hESC with primary antibodies followed by GAM antibodies failed to induce a similar cytotoxic effect as mAb 84 (FIG. 10B).

Discussion

The identification of cell surface antigens is important to hESC research because it is an invaluable tool for monitoring pluripotency and the development of specific cell populations during differentiation. Furthermore, because it is non-invasive, antibodies specific to cell surface antigens can be used to purify subsets of cells within a heterogeneous pool for detailed analysis or cell transplantation. Several of such cell surface antigens routinely used to characterize pluripotent hESC are SSEA-3, SSEA-4, Tra-1-60 and Tra-1-81. Unhelpfully, these antigens are also present on human EC cells and a recent study by Draper et al. [21] found that the changes in expression of these antigens in hESC during differentiation are very similar to human EC cells. Thus to gain a better understanding of the regulation of self-renewal and pluripotency in hESC, there is a need to identify new cell surface antigens that are uniquely expressed on hESC, which will be able to distinguish hESC from human EC cells.

In the studies described herein, live hESC were used for immunization of mice and after primary screening of the hybridomas for mAbs that bind to hESC surface markers, a panel of 10 mAbs was identified. Unlike SSEA-4 and Tra-1-60/81 which reacted strongly to both hESC and human EC cells, 5 of our antibodies (mAb 84, 95, 375, 432, 529) reacted strongly only with hESC and were negative or weakly reacting to human EC cells. Furthermore, antibody binding correlates with Oct-4 expression and is down-regulated as the hESC differentiate to form EB. These data strongly support the presence of antigens that are uniquely present on undifferentiated hESC. Moreover, when the entire mAb panel was screened against the H1 hESC line (data not shown), we found that the reactivity profile was similar to that of HES-2, 3 and 4 suggesting that the mAbs bind to antigens that are conserved across the different hESC lines.

Uniquely, mAb 84 not only bound to hESC but is also cytotoxic to the cells within 15-30 min of incubation. Unlike other cytotoxic mAbs that may require either the activation of complement or hypercross-linking to induce cell death [20, 22], mAb 84 mediated-killing of hESC is independent of both mechanisms. By IP and MS analysis, we identified podocalyxin-like protein-1 (PODXL) as the target antigen of mAb84 on hESC.

PODXL is a heavily glycosylated type-I transmembrane protein belonging to the CD34 family of sialomucins, which include CD34 and endoglycan [23,24]. PODXL was originally described as the major sialoprotein on podocytes of the kidney glomerulus [25] but was later found to be expressed on vascular endothelial cells and early hematopoietic progenitors [26,27]. More recently, PODXL has been implicated as an indicator of tumor aggressiveness in breast, liver and prostate cancers [28-30]. Human PODXL is located on chromosome 7q32-q33 and encodes for a mature protein of 528 amino acids [31]. However, because the extracellular domain of PODXL is extensively glycosylated with sialylated O-linked carbohydrates and 5 potential sites for N-linked glycosylation, the approximate molecular weight of PODXL is 160-165 kDa [32].

Functionally, PODXL has been reported to have quite diverse roles depending on the cell type in which it is expressed. In podocytes, PODXL acts as an anti-adhesion molecule that maintains the filtration slits open between podocyte foot processes by charge repulsion [33]. However, in high endothelial venules, PODXL acts as an adhesion molecule binding to L-selectin and mediating the tethering and rolling of lymphocytes [23]. In hESC, PODXL was identified transcriptionally as one of the genes highly expressed in undifferentiated hESC [34,35]. By EST frequency analysis, the level of PODXL expression was down-regulated by almost 2.5 fold in 7-8 day EB and approximately 7 and 12 fold in neuroectoderm-like cells and hepatocyte-like cells respectively [34]. This result was supported by immunohistochemistry of hESC and 8 day EB where staining was significantly reduced in the latter [36]. In a separate study, Wei et al. compared the transcriptome profile of hESC and mESC and observed that the expression of PODXL was not detected by MPSS in mESC line E-14 compared to hESC [37]. Taken together, these reports of PODXL expression in ESC correspond with our observations of mAb 84 by flow cytometry where binding reactivity was reduced in day 8 EB compared to undifferentiated hESC and absent in mESC. Concomitantly, the decrease or loss in mAb 84-mediated killing on FGF2-starved hESC and day 22 EB respectively can be attributed to the down-regulation of PODXL expression upon differentiation. Nevertheless, despite these reports on the expression of PODXL in undifferentiated hESC, its function has not been elucidated.

The mechanism responsible for hESC-killing by mAb 84 after binding to PODXL is also intriguing. In a report by Zhang et al. [38], an IgM mAb that targets the cell surface receptor, Porimin (Pro-oncosis receptor inducing membrane injury), was able to induce cell death in Jurkat cells by a process called oncosis [39]. Porimin, like PODXL, is a member of the mucin family because it has multiple O- and N-linked glycosylation sites on the extracellular domain of the protein [40]. Incubation of Jurkat cells with anti-Porimin resulted in rapid cell aggregation in suspension and an increased membrane permeability in >75% of cells after only 20 min of incubation. Cell killing was also independent of complement and temperature. Distinct from apoptosis, no DNA fragmentation or apoptotic bodies were observed after incubation with the mAb. By scanning electron microscope, anti-Porimin treated cells were found to have increased membrane pores, blebs and surface wrinkling. Comparing this with our data, it is surprising that mAb 84 and anti-Porimin share many similar hallmarks of cell killing. Additionally, preliminary results from our group found that mAb 84-treated cells did not exhibit elevated level of caspases, a characteristic of apoptosis. Thus, without being bound by theory, we hypothesize that mAb 84-mediated killing of hESC is due to a mechanism similar to oncosis.

The use of hESC as a starting source of material for differentiation to any cell type in the body has significant benefits to regenerative medicine. However, one of the major concerns after differentiation is the elimination of residual undifferentiated hESC prior to transplantation because these cells are tumorigenic. Previous work has shown that as few as two ESC implanted into nude mice resulted in the formation of teratomas, and grafting of in vitro differentiated ES cells did not alleviate the situation either [41,42]. Moreover, Cooke et al. reported that the site in which hESC were grafted influences the outcome of the teratomas formed. Large tumours of immature cells expressing the pluripotent marker SSEA-3 were predominant in grafts to the liver whilst smaller tumours of differentiated tissues were prevalent in subcutaneous implants [9]. Several different strategies have been developed to overcome this issue. In two separate studies, Chung et al. [8] and Fukuda et al. [43] demonstrated that recombinant mouse ESC lines carrying the sox1-GFP reporter gene could be used to purify sox1$^+$/GFP$^+$ differentiated neural precursors from ESC by fluorescent activated cell sorting (FACS). Transplantation of the purified cells did not result in teratoma formation whilst sox1$^-$/GFP$^-$ cells did. In hESC, Hewitt et al. engineered a line expressing α1,3 galactosyltransferase (GalT) under the control of the hTert promoter [44]. Undifferentiated hESC will express GalT which in turn catalyses and presents the α-gal epitope on the cell surface. The presence of the epitope will render the cells susceptible to circulating antibodies in human serum resulting in cell death in vitro. Despite the success of these strategies, they all require the generation of recombinant ESC lines carrying a selectable gene. By contrast, we have now demonstrated that non-manipulated undifferentiated hESC can be rapidly eliminated following incubation with mAb 84 in vitro. Currently, in vivo studies are ongoing to demonstrate the absence or reduction of tumor formation by hESC after mAb treatment. Additionally, we also propose that several of the other hESC-specific mAbs in our panel be used in combination with mAb 84 to ensure the complete removal of residual hESC that may survive mAb 84 killing due to the down-regulated expression of PODXL.

In conclusion, this is the first report of a cytotoxic mAb that selectively binds and kills undifferentiated hESC. Potentially, mAb 84 may be used prior to cell transplantation to eliminate residual hESC thus increasing the success and safety of the graft.

REFERENCE LIST

1. Thomson J A, Itskovitz-Eldor J, Shapiro S S et al. Embryonic stem cell lines derived from human blastocysts. Science 1998; 282:1145-1147.
2. Reubinoff B E, Pera M F, Fong C Y et al. Embryonic stem cell lines from human blastocysts: somatic differentiation in vitro. Nat. Biotechnol. 2000; 18:399-404.
3. Chambers I, Colby D, Robertson M et al. Functional expression cloning of Nanog, a pluripotency sustaining factor in embryonic stem cells. Cell 2003; 113:643-655.
4. Mitsui K, Tokuzawa Y, Itoh H et al. The homeoprotein Nanog is required for maintenance of pluripotency in mouse epiblast and ES cells. Cell 2003; 113:631-642.
5. Kannagi R, Cochran N A, Ishigami F et al. Stage-specific embryonic antigens (SSEA-3 and -4) are epitopes of a unique globo-series ganglioside isolated from human teratocarcinoma cells. EMBO J. 1983; 2:2355-2361.
6. Andrews P W, Banting G, Damjanov I et al. Three monoclonal antibodies defining distinct differentiation antigens associated with different high molecular weight polypeptides on the surface of human embryonal carcinoma cells. Hybridoma 1984; 3:347-361.
7. Son Y S, Park J H, Kang Y K et al. Heat Shock 70-kDa Protein 8 Isoform 1 is expressed on the surface of human embryonic stem cells and downregulated upon differentiation. Stem Cells 2005; 23:1502-1513.
8. Chung S, Shin B S, Hedlund E et al. Genetic selection of sox1GFP-expressing neural precursors removes residual tumorigenic pluripotent stem cells and attenuates tumor formation after transplantation. J. Neurochem. 2006; 97:1467-1480.
9. Cooke M J, Stojkovic M, Przyborski S A. Growth of teratomas derived from human pluripotent stem cells is influenced by the graft site. Stem Cells Dev. 2006; 15:254-259.
10. Choo A, Padmanabhan J, Chin A et al. Immortalized feeders for the scale-up of human embryonic stem cells in feeder and feeder-free conditions. J. Biotechnol. 2006; 122:130-141.
11. Choo A B, Padmanabhan J, Chin A C et al. Expansion of pluripotent human embryonic stem cells on human feeders. Biotechnol. Bioeng. 2004; 88:321-331.
12. Yin Y, Lim Y K, Salto-Tellez M et al. AFP(+), ESC-derived cells engraft and differentiate into hepatocytes in vivo. Stem Cells 2002; 20:338-346.
13. Doetschman T, Gregg R G, Maeda N et al. Targetted correction of a mutant HPRT gene in mouse embryonic stem cells. Nature 1987; 330:576-578.
14. Oh S K, Fong W J, Teo Y et al. High density cultures of embryonic stem cells. Biotechnol. Bioeng. 2005; 91:523-533.
15. Andrews P W, Bronson D L, Benham F et al. A comparative study of eight cell lines derived from human testicular teratocarcinoma. Int. J. Cancer 1980; 26:269-280.
16. Heins N, Lindahl A, Karlsson U et al. Clonal derivation and characterization of human embryonic stem cell lines. J. Biotechnol. 2006; 122:511-520.
17. Laemmli U K. Cleavage of structural proteins during the assembly of the head of bacteriophage T4. Nature 1970; 227:680-685.
18. Towbin H, Staehelin T, Gordon J. Electrophoretic transfer of proteins from polyacrylamide gels to nitrocellulose sheets: procedure and some applications. Proc. Natl. Acad. Sci. U.S.A 1979; 76:4350-4354.
19. Chaouchi N, Vazquez A, Galanaud P et al. B cell antigen receptor-mediated apoptosis. Importance of accessory molecules CD19 and CD22, and of surface IgM cross-linking. J. Immunol. 1995; 154:3096-3104.
20. Shan D, Ledbetter J A, Press O W. Apoptosis of malignant human B cells by ligation of CD20 with monoclonal antibodies. Blood 1998; 91:1644-1652.

21. Draper J S, Pigott C, Thomson J A et al. Surface antigens of human embryonic stem cells: changes upon differentiation in culture. J. Anat. 2002; 200:249-258.
22. Ball E D, Kadushin J M, Schacter B et al. Studies on the ability of monoclonal antibodies to selectively mediate complement-dependent cytotoxicity of human myelogenous leukemia blast cells. J. Immunol. 1982; 128:1476-1481.
23. Sassetti C, Tangemann K, Singer M S et al. Identification of podocalyxin-like protein as a high endothelial venule ligand for L-selectin: parallels to CD34. J. Exp. Med. 1998; 187:1965-1975.
24. Sassetti C, Van Zante A, Rosen S D. Identification of endoglycan, a member of the CD34/podocalyxin family of sialomucins. J. Biol. Chem. 2000; 275:9001-9010.
25. Kerjaschki D, Sharkey D J, Farquhar M G. Identification and characterization of podocalyxin—the major sialoprotein of the renal glomerular epithelial cell. J. Cell Biol. 1984; 98:1591-1596.
26. Kershaw D B, Thomas P E, Wharram B L et al. Molecular cloning, expression, and characterization of podocalyxin-like protein 1 from rabbit as a transmembrane protein of glomerular podocytes and vascular endothelium. J. Biol. Chem. 1995; 270:29439-29446.
27. Doyonnas R, Nielsen J S, Chelliah S et al. Podocalyxin is a CD34-related marker of murine hematopoietic stem cells and embryonic erythroid cells. Blood 2005; 105:4170-4178.
28. Casey G, Neville P J, Liu X et al. Podocalyxin variants and risk of prostate cancer and tumor aggressiveness. Hum. Mol. Genet. 2006; 15:735-741.
29. Chen X, Higgins J, Cheung S T et al. Novel endothelial cell markers in hepatocellular carcinoma. Mod. Pathol. 2004; 17:1198-1210.
30. Somasiri A, Nielsen J S, Makretsov N et al. Overexpression of the anti-adhesin podocalyxin is an independent predictor of breast cancer progression. Cancer Res. 2004; 64:5068-5073.
31. Kershaw D B, Wiggins J E, Wharram B L et al. Assignment of the human podocalyxin-like protein (PODXL) gene to 7q32-q33. Genomics 1997; 45:239-240.
32. Kershaw D B, Beck S G, Wharram B L et al. Molecular cloning and characterization of human podocalyxin-like protein. Orthologous relationship to rabbit PCLP1 and rat podocalyxin. J. Biol. Chem. 1997; 272:15708-15714.
33. Takeda T, Go W Y, Orlando R A et al. Expression of podocalyxin inhibits cell-cell adhesion and modifies junctional properties in Madin-Darby canine kidney cells. Mol. Biol. Cell 2000; 11:3219-3232.
34. Brandenberger R, Wei H, Zhang S et al. Transcriptome characterization elucidates signaling networks that control human ES cell growth and differentiation. Nat. Biotechnol. 2004; 22:707-716.
35. Cai J, Chen J, Liu Y et al. Assessing self-renewal and differentiation in human embryonic stem cell lines. Stem Cells 2006; 24:516-530.
36. Cai J, Olson J M, Rao M S et al. Development of antibodies to human embryonic stem cell antigens. BMC. Dev. Biol. 2005; 5:26.
37. Wei C L, Miura T, Robson P et al. Transcriptome profiling of human and murine ESCs identifies divergent paths required to maintain the stem cell state. Stem Cells 2005; 23:166-185.
38. Zhang C, Xu Y, Gu J et al. A cell surface receptor defined by a mAb mediates a unique type of cell death similar to oncosis. Proc. Natl. Acad. Sci. U.S.A 1998; 95:6290-6295.
39. Majno G, Joris I. Apoptosis, oncosis, and necrosis. An overview of cell death. Am. J. Pathol. 1995; 146:3-15.
40. Ma F, Zhang C, Prasad K V et al. Molecular cloning of Porimin, a novel cell surface receptor mediating oncotic cell death. Proc. Natl. Acad. Sci. U.S.A 2001; 98:9778-9783.
41. Harkany T, Andang M, Kingma H J et al. Region-specific generation of functional neurons from naive embryonic stem cells in adult brain. J. Neurochem. 2004; 88:1229-1239.
42. Lawrenz B, Schiller H, Willbold E et al. Highly sensitive biosafety model for stem-cell-derived grafts. Cytotherapy. 2004; 6:212-222.
43. Fukuda H, Takahashi J, Watanabe K et al. Fluorescence-activated cell sorting-based purification of embryonic stem cell-derived neural precursors averts tumor folination after transplantation. Stem Cells 2006; 24:763-771.
44. Hewitt Z, Priddle H, Thomson A et al. Ablation of undifferentiated human embryonic stem cells: exploiting innate immunity against the Gal {alpha}1-3Gal{beta}1-4GlcNAc-R ({alpha}-gal) epitope. Stem Cells 2006;2005-0481.

TABLE I

Summary of mAb Reactivity to Different Cell Lines

| | | hESC | | | | Feeders | mESC | | EC | | | Misc | |
|---|---|---|---|---|---|---|---|---|---|---|---|---|---|
| mAb Clone | Isotype | HES-3 | HES-3 EB | HES-2 | HES-4 | E-MEF | CS-1 | E-14 | Ntera | 2102Ep | NCCIT | HEK-293 | HeLa |
| 84 | IgM | +++ | +/− | ++++ | ++ | − | − | − | − | − | + | − | − |
| 95 | IgM | ++ | − | ++++ | ++ | − | − | − | − | − | +/− | − | − |
| 375 | IgM | +++ | −[a] | +++ | Nd | − | − | − | Nd | − | − | − | − |
| 432 | IgM | +++ | −[a] | +++ | Nd | − | − | − | Nd | − | − | − | − |
| 529 | IgM | +++ | −[a] | +++ | Nd | − | − | − | Nd | − | − | − | − |
| 14 | IgM | ++ | + | ++++ | ++ | − | ++ | − | ++ | + | − | − | − |
| 85 | IgM | ++ | +/− | ++++ | ++++ | − | − | − | ++++ | + | ++ | − | − |
| 8 | IgG$_{2a}$ | ++++ | + | ++++ | ++ | − | − | − | + | +++ | + | + | + |
| 5 | IgM | + | + | + | + | − | − | − | ++ | + | + | +++ | ++++ |
| 63 | IgM | ++ | ++ | +++ | ++ | − | − | − | +++ | + | + | ++ | ++++ |
| SSEA-4 | IgM | +++ | Nd | ++++ | +++ | + | + | + | +++ | ++ | +++ | + | + |
| Tra-1-60 | IgM | +++ | Nd | ++++ | ++++ | − | − | − | ++++ | ++ | +++ | − | − |
| Tra-1-81 | IgM | +++ | Nd | ++++ | ++++ | − | − | − | ++++ | ++ | +++ | − | − |

+ represents binding; +/− represents partial/weak binding; − represents no binding; Nd represents not determined
[a]Day 22 EB were used instead of day 8 EB

What is claimed is:

1. A kit comprising an antibody that specifically binds PODXL on the surface of a cell, and which is cytotoxic to said cell, and an agent that detects a human embryonic stem cell marker, wherein the antibody comprises (a) at least one light chain variable region comprising the following complementarity determining regions (CDRs):

(i) SASSSVNYMY, (SEQ ID NO: 2)

(ii) DTSNLAS, (SEQ ID NO: 3)

(iii) QQWSSYPYT; (SEQ ID NO: 4)
and (b) at least one heavy chain variable region comprising the following CDRs:

(iv) NYWMN, (SEQ ID NO: 5)

(v) EIRLKSNNYATHYAESVKG, (SEQ ID NO: 6)
and (vi) ERA. (SEQ ID NO: 7)

2. The kit according to claim 1 wherein the human embryonic stem cell marker is selected from the group consisting of Oct 4, SSEA-4, Tra-1-60, Tra-1-81 and GCTM-2.

3. The kit according to claim 1, comprising at least 5 µg of the antibody.

4. The kit according to claim 1 wherein the antibody has at least one light chain variable region comprising the amino acid sequence of SEQ ID NO: 8.

5. The kit according to claim 1 wherein the antibody has at least one heavy chain variable region comprising the amino acid sequence of SEQ ID NO: 10.

* * * * *